United States Patent
Tsuchiya et al.

(10) Patent No.: US 10,751,211 B2
(45) Date of Patent: Aug. 25, 2020

(54) KNEE SUPPORTER

(71) Applicants: KOWA COMPANY, LTD., Nagoya-shi (JP); ADVANCING INC., Osaka-shi (JP); DMCHAIN COOPERATIVE, Kahoku-shi (JP)

(72) Inventors: Akiharu Tsuchiya, Chuo-ku (JP); Kenta Tsuzuranuki, Chuo-ku (JP); Hitoshi Ojima, Osaka (JP); Hidenori Kaseno, Kahoku (JP)

(73) Assignees: KOWA COMPANY, LTD., Nagoya-shi (JP); ADVANCING INC., Osaka-shi (JP); DMCHAIN COOPERATIVE, Kahoku-shi (JP)

( * ) Notice: Subject to any disclaimer, the term of this patent is extended or adjusted under 35 U.S.C. 154(b) by 978 days.

(21) Appl. No.: 15/123,612

(22) PCT Filed: Mar. 3, 2015

(86) PCT No.: PCT/JP2015/056222
§ 371 (c)(1),
(2) Date: Sep. 2, 2016

(87) PCT Pub. No.: WO2015/133479
PCT Pub. Date: Sep. 11, 2015

(65) Prior Publication Data
US 2017/0071773 A1 Mar. 16, 2017

(30) Foreign Application Priority Data

Mar. 3, 2014 (JP) .................................. 2014-040935
Mar. 6, 2014 (JP) .................................. 2014-043638
Dec. 26, 2014 (JP) .................................. 2014-266458

(51) Int. Cl.
*A61F 5/00* (2006.01)
*A61F 13/00* (2006.01)
(Continued)

(52) U.S. Cl.
CPC .......... *A61F 5/0106* (2013.01); *A61F 13/061* (2013.01); *A61F 13/062* (2013.01)

(58) Field of Classification Search
CPC ........ A61F 13/061; A61F 13/062; A61F 5/01; A61F 13/08; A61F 5/0109; A61F 5/0125;
(Continued)

(56) References Cited

U.S. PATENT DOCUMENTS 5,507,722 A * 4/1996 Richardson ........... A61F 2/7812
602/60
5,656,023 A * 8/1997 Caprio, Jr. ............ A61F 5/0106
602/26

(Continued)

FOREIGN PATENT DOCUMENTS

EP 2 399 553 A2 12/2011
JP 1-150915 U 10/1989
(Continued)

OTHER PUBLICATIONS

Extended European Search Report dated Sep. 8, 2017 in Patent Application No. 15757896.4.
(Continued)

*Primary Examiner* — Kim M Lewis
(74) *Attorney, Agent, or Firm* — Oblon, McClelland, Maier & Neustadt, L.L.P.

(57) ABSTRACT

A knee joint supporter includes a first anchor having a loop face, a main body including second anchor, first supporting and second supporting, connections joining the anchors and connecting the first anchor and main body, a first engaging joined to the second supporting and having a hook face to stick to the loop face, a second engaging joined to the first anchor and having a hook face to stick to the loop face, and a third engaging joined to the first supporting and having a hook face to the loop face. The first anchor fastens around (Continued)

a thigh of a wear. The second anchor extends below popliteal region. The first supporting extends on one side from below part corresponding to a patella, and the second supporting extends on the other side of the part corresponding to the patella and crosses the first supporting below the part corresponding to the patella.

18 Claims, 20 Drawing Sheets

(51) Int. Cl.
*A61F 5/01* (2006.01)
*A61F 13/06* (2006.01)

(58) Field of Classification Search
CPC .. A61F 5/013; A61F 13/00051; A61F 13/085; A61F 2002/4435; A61F 2/442; A61F 2/68; A61F 5/0111; A61F 5/0123; A61F 2002/30062; A61F 2002/30462; A61F 2002/305; A61F 2002/6827; A61F 2005/0176; A61F 2210/0004; A61F 2/08; A61F 2/441; A61F 5/0102; A61F 5/05816; A61F 5/37; A61F 13/00; A61F 13/00063; A61F 13/02; A61F 13/0206; A61F 13/0226; A61F 13/023; A61F 13/0253; A61F 13/0273; A61F 13/06; A61F 13/148; A61F 2002/2817; A61F 2002/3008; A61F 2002/30133; A61F 2002/30176; A61F 2002/30451; A61F 2002/30461; A61F 2002/30471; A61F 2002/30479; A61F 2002/30578; A61F 2002/30579; A61F 2002/30677; A61F 2002/30738; A61F 2002/30785; A61F 2002/30787; A61F 2002/30841; A61F 2002/3085; A61F 2002/30884; A61F 2002/30892; A61F 2002/30925; A61F 2002/3093; A61F 2002/30932; A61F 2002/444; A61F 2002/448; A61F 2002/4495; A61F 2002/5012; A61F 2002/5016; A61F 2002/5056; A61F 2002/74; A61F 2005/0134; A61F 2005/0141; A61F 2005/0155; A61F 2005/0158; A61F 2005/0165; A61F 2005/0167; A61F 2005/0169; A61F 2005/0179; A61F 2005/0188; A61F 2007/0032; A61F 2007/004; A61F 2007/0042; A61F 2007/0044; A61F 2007/0055; A61F 2007/0091; A61F 2007/0093; A61F 2007/0094; A61F 2007/0219; A61F 2007/0225; A61F 2007/0228; A61F 2007/0231; A61F 2007/0239; A61F 2007/108; A61F 2220/0025; A61F 2220/0058; A61F 2220/0075; A61F 2220/0091; A61F 2230/0015; A61F 2230/0054; A61F 2230/0069; A61F 2250/0067; A61F 2250/0098; A61F 2310/00017; A61F 2310/00023; A61F 2310/00029; A61F 2310/00293; A61F 2310/00359; A61F 2310/00407; A61F 2310/00796; A61F 2310/00976; A61F 2/0063; A61F 2/0811; A61F 2/28; A61F 2/30749; A61F 2/3836; A61F 2/3859; A61F 2/389; A61F 2/4405; A61F 2/4455; A61F 2/4465; A61F 2/447; A61F 2/4611; A61F 2/50; A61F 2/583; A61F 2/586; A61F 5/00; A61F 5/0003; A61F 5/0106; A61F 5/012; A61F 5/0127; A61F 5/0193; A61F 5/0195; A61F 5/05858; A61F 5/14; A61F 5/30; A61F 5/32; A61F 5/34; A61F 5/3723; A61F 7/0085; A61F 7/02; A61F 7/08; A61F 9/0017; A61F 9/00772; B29C 66/71; B29C 65/18; B29C 66/431; B29C 65/022; B29C 66/1122; B29C 66/1282; B29C 66/12841; B29C 66/133; B29C 66/14; B29C 66/244; B29C 66/303; B29C 66/30326; B29C 66/43; B29C 66/433; B29C 66/45; B29C 66/472; B29C 66/4722; B29C 66/4724; B29C 66/723; B29C 66/727; B29C 66/729; B29C 66/7294; B29C 66/7392; B29C 66/73921; B29C 66/7394; B29C 66/81422; B29C 66/81423; B29C 66/81435; B29C 66/8226; B29C 66/83221; B29C 66/8362; B29C 65/606; B29C 66/20; B29C 66/3032
USPC ............................ D24/192; 602/26, 27–29
See application file for complete search history.

(56) References Cited

U.S. PATENT DOCUMENTS

| | | | |
|---|---|---|---|
| 5,860,945 A * | 1/1999 | Cramer | A61F 5/0106 602/62 |
| 2003/0204156 A1 | 10/2003 | Nelson et al. | |
| 2007/0185425 A1 | 8/2007 | Einarsson et al. | |
| 2007/0219478 A1 * | 9/2007 | Powers | A61F 5/0104 602/62 |
| 2011/0319800 A1 | 12/2011 | Matsunaga | |
| 2014/0243755 A1 * | 8/2014 | Slemmen | A61M 5/3202 604/198 |
| 2014/0378883 A1 * | 12/2014 | Cooper | A61F 5/0109 602/26 |
| 2015/0290013 A1 * | 10/2015 | Mueller | A61F 5/0123 602/26 |
| 2015/0290046 A1 * | 10/2015 | Novick | A61F 5/0106 602/26 |
| 2016/0367390 A1 * | 12/2016 | Nordt, III | A61F 5/0104 |

FOREIGN PATENT DOCUMENTS

| | | |
|---|---|---|
| JP | 2000-342612 A | 12/2000 |
| JP | 2005-168532 A | 6/2005 |
| JP | 2006-6375 A | 1/2006 |
| JP | 2009-211268 A | 9/2009 |
| JP | 2011-45628 A | 3/2011 |
| JP | 2012-143311 A | 8/2012 |
| JP | 2014-152425 A | 8/2014 |

OTHER PUBLICATIONS

International Search Report dated May 12, 2015 in PCT/JP15/056222 Filed Mar. 3, 2015.

* cited by examiner

Fig. 4
(a)
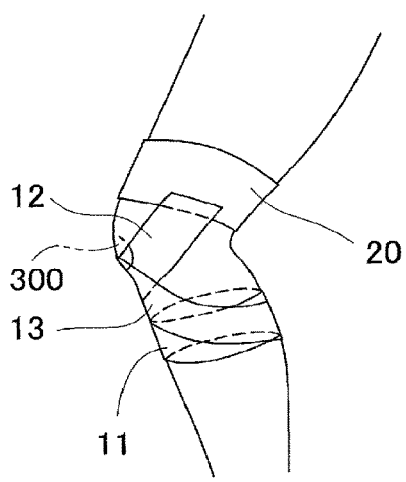
(b)
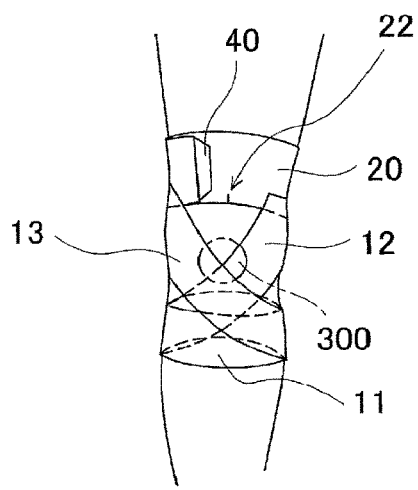
(c)
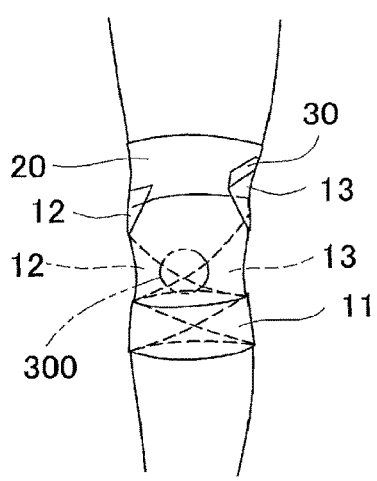
(d)
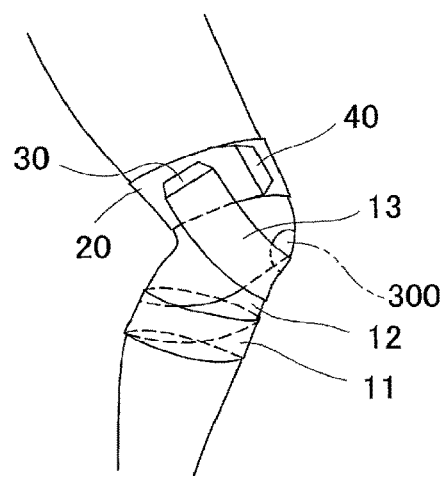

Fig. 10

| Evaluation items | Comparative Example 1 (35%) | Example 1 (45%) | Example 2 (60%) | Example 3 (75%) | Comparative Example 2 (90%) |
|---|---|---|---|---|---|
| ① Fixing force | Considerably strong (2.6 points) | Strong (2.0 points) | Strong (1.8 points) | Weak (1.2 points) | Weak (1.0 points) |
| ② Pain | Painful (1.0 points) | Painful (1.2 points) | Almost painless (1.6 points) | Almost painless (1.6 points) | Painless (2.0 points) |
| ③ Ease of peeling-off of touch fastener | Good (3.0 points) | Good (2.8 points) | Good (2.8 points) | Slightly poor (2.2 points) | Poor (1.2 points) |
| ④ Close contact property of fabric | With floating (1.0 points) | With floating (1.2 points) | Very good (2.8 points) | Very good (3.0 points) | Very good (3.0 points) |
| ⑤ Ease of winding | Hard to wind tightly (1.2 points) | Easy to wind (2.4 points) | Very easy to wind (2.6 points) | Easy to wind (2.4 points) | Extended too much, and thus hard to wind (1.2 points) |
| ⑥ Ease of adjustment of fixing force | Hard to adjust tightly (1.0 points) | Easy to adjust (2.0 points) | Very easy to adjust (2.6 points) | Very easy to adjust (2.6 points) | Very easy to adjust (2.6 points) |
| ⑦ Difficulty of fabric folding | Hard to be folded (3.0 points) | Hard to be folded (3.0 points) | Hard to be folded (2.8 points) | Slightly easy to be folded (2.2 points) | Easy to be folded (1.2 points) |
| Total points | 12.8 points | 14.6 points | 17.0 points | 15.2 points | 12.2 points |
| Average score | 1.83 points | 2.09 points | 2.43 points | 2.17 points | 1.74 points |

Fig. 13
(a)
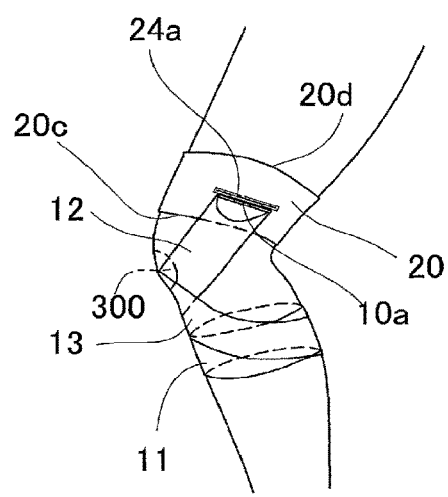
(b)
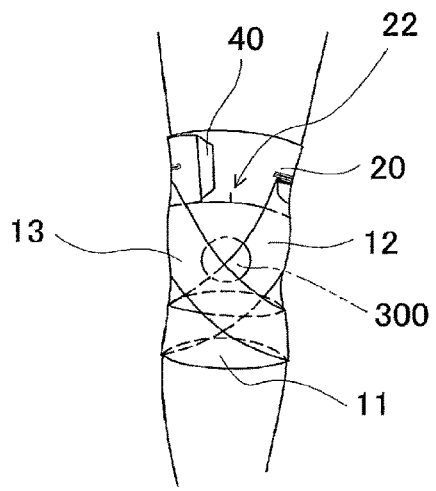
(c)
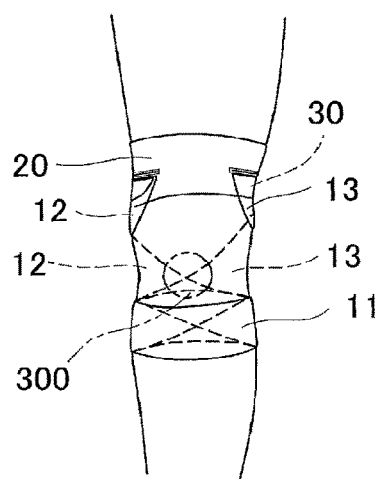
(d)
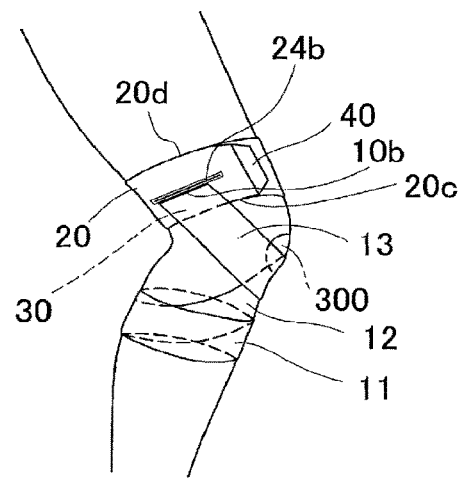

Fig. 18
(a)
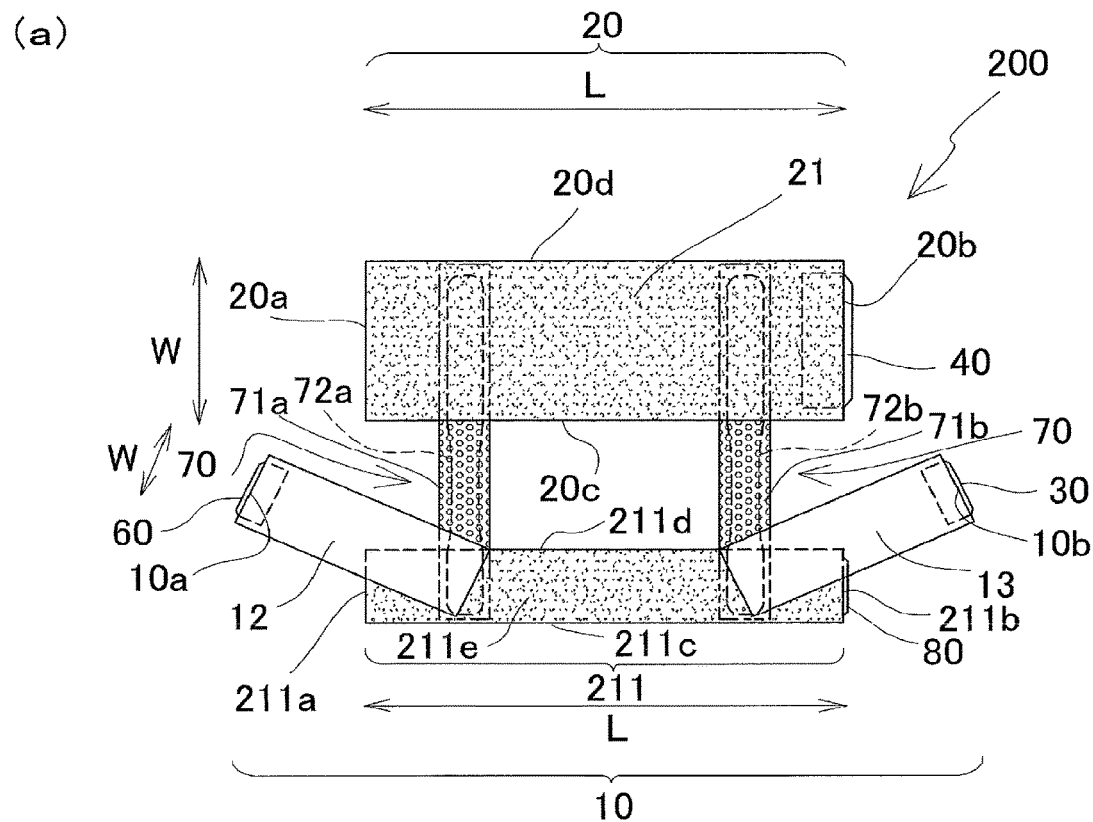
(a)
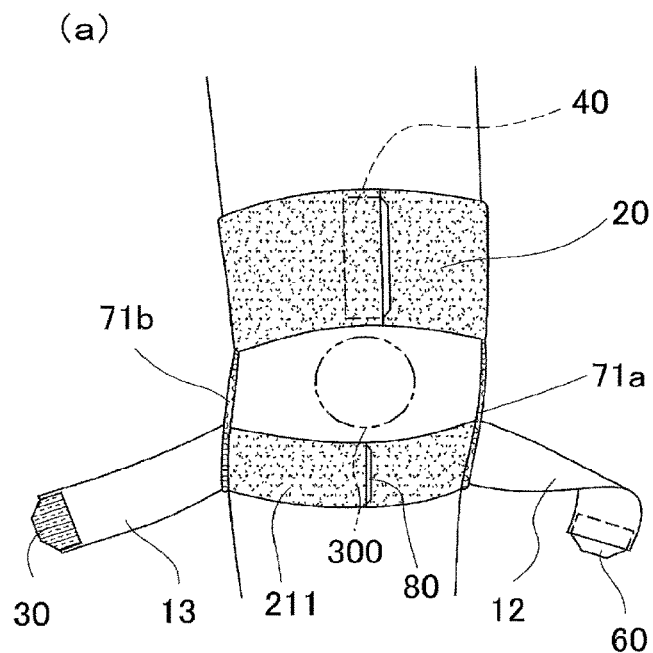

KNEE SUPPORTER

TECHNICAL FIELD

The present invention relates to a knee supporter which can support the daily motion of a wearer, and a method for supporting the knee joint, and in particular, to a knee joint bandage or a knee joint supporter having a taping function of improving the stability of the knee joint, thereby reducing the fatigue of a wearer and reducing a load on the patellar tendon.

BACKGROUND ART

In the related art, a band-shaped taping tape (a stretchable or non-stretchable adhesive cloth tape which is used by being stuck to a part of the body), a bandage, a substantially tubular supporter knitted with circular knitting, or the like has been used in order to serve a medical purpose such as for prevention of an external injury such as a sprain of a wrist joint, an ankle joint, or a knee joint, emergency treatment at the time of the external injury, assistance in rehabilitation after the injury and until complete recovery, or prevention of recurrence of the external injury or the like.

Of these, the taping tape is disposable, thereby is not economical, and has a problem in which depending on the constitution of a user, a rash occurs on the skin of the user due to an adhesive, and there is a concern that in a user having a sensitive skin, such as an aged person, skin peeling may occur when peeling off the taping tape.

Further, the circular knitting supporter has an approximately tubular shape, and therefore, there is a problem in which there is a concern that in a case where an injured site is inserted therein to be forcedly bent, it may be painful, and a fixing force is inferior, as compared to the taping tape.

In contrast, the bandage is a band-shaped body having stretchability in a longitudinal direction, and therefore, it easily follows an affected area, the wearer themselves can wind it while adjusting a fixing force, an excessive force is not applied against the movement of the wearer's body, a stable fixing force can be obtained, and it is economical because it can be used repeatedly.

For example, a knee joint supporter of the related art is composed of a first band-shaped and stretchable belt having a pile function on one face thereof and having a joining portion which is joined to the pile function, at an end portion of the other face thereof, and a second band-shaped and stretchable belt having a pile function on one face thereof and having a joining portion which is joined to the pile function, at end portion of the other face thereof, in which the second belt is, at a base end portion thereof, mounted on the first belt at a predetermined angle (refer to PTL 1, for example).

Further, in a knee correction implement of the related art, a base end of a stretchable biasing band (a biasing part) is sewn to a place to which a base end of a spiral winding portion of an annular winding part is sewn, and an end face fastener of the tip of the biasing band (the biasing part) is locked to a connection end on the opposite side of the annular winding part. Then, the base end of the spiral winding part is biased toward the connection end from a biasing end by the biasing band, and accordingly, the spiral winding part is biased in a direction against the expansion and contraction direction thereof, and thus the correction implement is not loosened even if the leg is moved, and thereby, the correction effect is improved (refer to PTL 2, for example).

Further, in a knee joint supporter of the related art, an annular band and a spiral band configured of a material having stretchability and flexibility and a material having flexibility and stretchability and capable of being engaged with Magic tape (registered trademark) on the surface are combined and used, and kinetic dynamic action is utilized from the anatomical view point, whereby a sufficient supporting force and fixing force are obtained without using a reinforcing member such as a support stay which causes a sense of discomfort at the time of mounting (refer to PTL 3, for example).

Further, a knee supporter of the related art is configured to include a supporter main body which is provided with: a stretchable inner fastening belt which is wrapped from the outside below the patellar to the lower rear side of the thigh through the inside of the knee joint; and a stretchable outer fastening belt which is wrapped from the inside below the patellar to the lower rear side of the thigh through the outside of the knee joint, and the inner fastening belt is formed using a material having relatively high stretchability, as compared to the outer fastening belt (refer to PTL 4, for example).

Further, a knee joint supporter of the related art is provided with: a main body made of an elastic cloth covering a thigh part, a lower leg part, and a knee joint part; stays disposed over an area from the upper side of the thigh part to the lower side of the lower leg part at the right and left of the surface of the main body; stay covers respectively provided at a thigh part and a lower leg part of the main body so as to cover the stays; a non-stretchable or poorly-stretchable lower leg part front belt which is, at one end, mounted on the upper side of either one of the stay covers of the lower leg part and can be, at the other end, coupled to a metal fitting mounted on the upper side of the other stay cover, so as to pass over the tibial tuberosity; a non-stretchable or poorly-stretchable lower leg part back belt which is, at one end, mounted on either one of the stay covers of the lower leg part and can be, at the other end, coupled to a metal fitting mounted on the other stay cover, so as to pass through the back of the lower leg part; a non-stretchable or poorly-stretchable thigh part back belt which is, at one end, mounted on either one of the stay covers of the thigh part and can be, at the other end, coupled to a metal fitting mounted on the other stay cover, so as to pass through the back of the thigh part; and two stretchable auxiliary belts, each of which is, at one end, mounted on the lower side of each of the right and left stay covers of the lower leg part, and which extend diagonally upward so as to cross each other on the tibial tuberosity and lead to the thigh part (refer to PTL 5, for example).

CITATION LIST

Patent Literature

[PTL 1] JP-A-2006-6375
[PTL 2] JP-A-2011-45628
[PTL 3] JP-A-2005-168532
[PTL 4] JP-A-2012-143311
[PTL 5] JP-UM-A-1-150915

SUMMARY OF INVENTION

Technical Problem

In the knee joint supporter of the related art disclosed in PTL 1, the second belt is wound from an internal rotation direction of the lower leg while being pulled downward and is fixed by joining the joining portion to the pile function formed on one face of the second belt, whereby tension is always applied inward against an outward twist of the tibia, and thus a force pulling back in the opposite direction acts such that the femur is not twisted inward and the tibia is not twisted outward. For this reason, the knee joint supporter of the related art lacks the balance of the tension by the second belt which is applied to the outer surface and the inner surface of the leg, and is neither for improving the stability of the knee joint, nor reducing the fatigue of a wearer.

Further, in PTL 1, there is no specific disclosure of the maximum elongation (the percentage of the difference between the longest length (an elongation dimension) when having been stretched with the highest load and the original length (a lay-flat size) with respect to the original length) of each of the first belt and the second belt.

Further, in the knee correction implement of the related art disclosed in PTL 2, almost half of the tip of the spiral winding part is wound to circle around the leg, a circling and winding portion of almost half of the tip of the spiral winding part fulfills the same function as the annular winding part, and the spiral winding part is spirally wound around the knee, thereby correcting the external rotation or the internal rotation of the knee, and the knee correction implement does not aim at taping for stabilizing the knee joint.

Further, in the knee correction implement of the related art, a material in which cloths (a hook-and-loop fastener cloth and a usual cloth) are joined and fixed to the front and back surfaces of a rubber plate is used for the annular winding part, and a material in which the periphery of a rubber plate is covered with a cloth is used for the spiral winding part. Therefore, there is a problem in which the thicknesses of the annular winding part and the spiral winding part become thicker.

Further, in PTL 2, there is no specific disclosure of the maximum elongation of each of the annular winding part and the spiral winding part.

Further, in the knee joint supporter of the related art disclosed in PTL 3, joining means and a joining position between the annular band (an upper band of the annular band or a lower band of the annular band) and the spiral band are unclear. However, as far as it is viewed from the drawings of PTL 3, it is considered that the spiral band is joined to the upper band of the annular band and is not joined to the lower band of the annular band. For this reason, although the upper band of the annular band functions as an upper anchor of the spiral band, the lower band of the annular band does not function as a lower anchor of the spiral band. Therefore, there is a problem in which the spiral band is shifted upward.

Further, in the knee supporter of the related art disclosed in PTL 4, a lower portion of the supporter main body is a lower tubular main body having a tubular shape, and therefore, in a case of mounting the knee supporter, it is necessary to insert the leg into the lower tubular main body from above in a state where an opening-closing flap has been opened, and due to an individual difference in the circumference of the lower leg, there is a limit to a size range.

Further, in the knee supporter of the related art, each of portions crossing each other below the patella in the inner fastening belt and the outer fastening belt is configured with a flap composed of a single sheet of stretchable cloth and is integrated, and therefore, the inner fastening belt and the outer fastening belt below the crossing portions do not independently act, and thus there is a problem in which it is not possible to sufficiently exhibit the effect of raising the patella of a wearer.

Further, in the knee joint supporter of the related art disclosed in PTL 5, both the auxiliary belts cross each other on the lower leg part front belt which is fitted to a lower portion of the patella and passes over the tibial tuberosity, and in a state where the knee is not flexed in the upright position, a moderate compression force is applied to the tibial tuberosity by the lower leg part front belt, thereby acting so as to constantly pull back the tibial tuberosity to a normal position, and if the knee is greatly flexed, a compression force on the tibial tuberosity is increased by the auxiliary belts, thereby acting so as to prevent the tibial tuberosity from trying to project forward. For this reason, in the knee joint supporter of the related art, the two auxiliary belts do not act so as to raise the patella of a wearer.

The present invention has been made in order to solve the problems as described above and has an object to provide a knee joint bandage or a knee joint supporter which improves the stability of the knee joint, thereby being able to reduce the fatigue of a wearer and reduce a load on the patellar tendon.

Solution to Problem

According to the present invention, there is provided a knee supporter including: a first anchor part which is woven in a fabric having a loop face of a touch fastener and is fastened around the thigh of a wearer; and a main body part which is woven in a band-shaped fabric and composed of a second anchor part which is disposed at least below the popliteal region of the wearer, a first supporting part which is disposed on one side of a part corresponding to the patella of the wearer, and a second supporting part which is disposed on the other side of the part corresponding to the patella of the wearer to cross the first supporting part below the part corresponding to the patella of the wearer.

In addition, a knee supporter is a broader concept which includes a knee joint bandage which includes a band-shaped fabric having stretchability in a warp direction as a main material, and a knee joint supporter in which a member associated with a band-shaped fabric is added to the band-shaped fabric.

According to the present invention, there is provided a knee joint bandage including: a band-shaped main body part which is woven in a fabric having a loop face of a touch fastener and is composed of a winding part which is wound around the lower leg of a wearer, a first supporting part which is disposed on one side of a part corresponding to the patella of the wearer, and a second supporting part which is disposed on the other side of the part corresponding to the patella of the wearer to cross the first supporting part below the part corresponding to the patella of the wearer; an anchor part which is joined to one end of the main body part, is woven in a fabric having a loop face of a touch fastener, and is fastened around the thigh of the wearer; and a first engaging part which is joined to the other end of the main body part and has a hook face of a touch fastener, which is detachably stuck to the loop face of the anchor part.

Further, in the knee joint bandage according to the present invention, as necessary, the first supporting part is provided on the one end side of the main body part, the second supporting part is provided on the other end side of the main body part, the winding part is provided between the first supporting part and the second supporting part, and the first supporting part, the winding part, and the second supporting part have straight line shapes having the same width.

Further, in the knee joint bandage according to the present invention, as necessary, a maximum elongation in a longitudinal direction of the main body part is in a range of 40% to 80%.

Further, in the knee joint bandage according to the present invention, as necessary, the first anchor part and the main body part are joined to each other with an angle between a circumferential direction of the first anchor part and a longitudinal direction of the main body part being in a range of 110° to 130°.

Further, in the knee joint bandage according to the present invention, as necessary, a joining portion between the first anchor part and one end of the main body part is sewn convexly to the other end side of the main body part so as to become longer than a length in a width direction of the main body part.

Further, in the knee joint bandage according to the present invention, as necessary, a width of the first anchor part is wider than a width of the main body part.

Further, in the knee joint bandage according to the present invention, as necessary, the first anchor part is a band-shaped body, a joining portion between the first anchor part and one end of the main body part is joined at a position where a distance from one end or the other end of the first anchor part corresponds to a length in a range of ¼ to ½ of a length of the first anchor part, and the first anchor part has, at one end or the other end, a second engaging part having a hook face of a touch fastener, which is detachably stuck to the loop face of the first anchor part.

Further, in the knee joint bandage according to the present invention, as necessary, the first anchor part is provided with a slit extending in a longitudinal direction of the main body part, at least between an upper side of the first anchor part and one end of the main body part in a state where the first anchor part has been fastened around the thigh of the wearer, and/or between the upper side of the first anchor part and the other end of the main body part in a state where the first engaging part has been engaged with the first anchor part.

Further, in the knee joint bandage according to the present invention, as necessary, a pattern composed of characters, figures, symbols, or a combination thereof is formed in a front ground face of the main body part.

According to the present invention, there is provided a knee joint supporter including: a first anchor part which is woven in a fabric having a loop face of a touch fastener and is fastened around the thigh of a wearer; a main body part which is a band-shaped fabric and is composed of a second anchor part which is disposed at least below the popliteal region of the wearer, a first supporting part which is disposed on one side from below a part corresponding to the patella of the wearer, and a second supporting part which is disposed on the other side of the part corresponding to the patella of the wearer to cross the first supporting part below the part corresponding to the patella of the wearer; connection parts which are joined to the first anchor part and the second anchor part, thereby integrating the first anchor part and the main body part; a first engaging part which is joined to an end portion of the second supporting part and has a hook face of a touch fastener, which is detachably stuck to the loop face of the first anchor part; a second engaging part which is joined to one end or the other end of the first anchor part and has a hook face of a touch fastener, which is detachably stuck to the loop face of the first anchor part; and a third engaging part which is joined to an end portion of the first supporting part and has a hook face of a touch fastener, which is detachably stuck to the loop face of the first anchor part.

Further, in the knee joint supporter according to the present invention, as necessary, the first supporting part is provided on the one end side of the main body part, the second supporting part is provided on the other end side of the main body part, the second anchor part is provided between the first supporting part and the second supporting part, and the main body part has a straight shape having an equal width.

Further, in the knee joint supporter according to the present invention, as necessary, the connection parts are a pair of left and right bag-shaped parts each containing a support and are disposed on both sides of the part corresponding to the patella of the wearer.

Further, in the knee joint supporter according to the present invention, as necessary, the connection parts are a pair of left and right bag-shaped parts each containing a support, and a covering part which covers an area surrounded by the pair of left and right bag-shaped parts, a lower side of the first anchor part, and an upper side of the second anchor part, and are disposed at the popliteal region of the wearer from both sides of the part corresponding to the patella of the wearer.

According to the present invention, there is provided a method for supporting a knee joint of a wearer by using a knee supporter provided with one or two band-shaped supporting parts having stretchability, including: mounting the knee supporter so as to raise the patella of the wearer from the lower side to the upper side by disposing the band-shaped supporting parts on both right and left sides from the lower side of a part corresponding to the patella of the wearer.

Further, in the method for supporting a knee joint according to the present invention, as necessary, the knee supporter is provided with a band-shaped anchor part having a loop face, which is fixed to the thigh of the wearer, and the knee supporter is mounted so as to raise the patella from the lower side to the upper side by making one end of each of the band-shaped supporting parts be engaged with the band-shaped anchor part.

Further, in the method for supporting a knee joint according to the present invention, as necessary, the knee supporter is provided with two band-shaped supporting parts having stretchability, and the knee supporter is mounted so as to raise the patella from the lower side to the upper side by crossing the two band-shaped supporting parts at the lower side of the part corresponding to the patella of the wearer.

In addition, in the following description of the present invention, the expression "being disposed" means "being placed to be applied to a predetermined position of a person (a site organ of a wearer)" and the wording "being disposed" is used to indicate this, the expression "being provided" means "being provided at a predetermined position of an object (a supporter)" and the wording "being provided" is used to indicate this.

Further, among the present inventions, the invention relating to the method for supporting a knee joint is not intended for medical practice, and a wearer of the knee supporter is also primarily intended for healthy people. That is, the method for supporting a knee joint according to the present invention aims at assistance in walking or going up and down stairs in the usual everyday life of a wearer, or prevention of injury, a reduction in fatigue, or the like during exercise.

Advantageous Effects of Invention

In the knee supporter, the knee joint bandage, the knee joint supporter, and the method for supporting a knee joint according to the present invention, due to gripping the knee region (the knee joint) of a wearer from the right and left by the main body part (the supporting parts), the knee region of the wearer is not deflected to the right and left more than necessary and stability can be secured. Further, in the knee supporter, the knee joint bandage, the knee joint supporter, and the method for supporting a knee joint according to the present invention, by supporting the knee region (the knee joint) of a wearer to raise it from the lower side to the upper side by the main body part (the supporting parts), it is possible to reduce a burden on the knee region of the wearer by smoothly assisting in the movement of the quadriceps muscle.

BRIEF DESCRIPTION OF DRAWINGS

FIG. 4(a) is an explanatory diagram of the wearing state of the knee joint bandage shown in FIGS. 1 and 3 when viewed from the right side, FIG. 4(b) is an explanatory diagram of the wearing state of the knee joint bandage shown in FIGS. 1 and 3 when viewed from the front side, FIG. 4(c) is an explanatory diagram of the wearing state of the knee joint bandage shown in FIGS. 1 and 3 when viewed from the back side, and FIG. 4(d) is an explanatory diagram of the wearing state of the knee joint bandage shown in FIGS. 1 and 3 when viewed from the left side.

FIG. 10 is a table showing the evaluation results of an effect feeling due to a difference in the maximum elongation of the main body part shown in FIG. 1.

FIG. 13(a) is an explanatory diagram of the wearing state of the knee joint bandage shown in FIGS. 11 and 12 when viewed from the right side, FIG. 13(b) is an explanatory diagram of the wearing state of the knee joint bandage shown in FIGS. 11 and 12 when viewed from the front side, FIG. 13(c) is an explanatory diagram of the wearing state of the knee joint bandage shown in FIGS. 11 and 12 when viewed from the back side, and FIG. 13(d) is an explanatory diagram of the wearing state of the knee joint bandage shown in FIGS. 11 and 12 when viewed from the left side.

FIG. 18(a) is a front view showing a schematic configuration of another knee joint supporter according to the third embodiment, and FIG. 18(b) is an explanatory diagram showing a state where a first anchor part of the knee joint supporter shown in FIG. 18(a) is fastened around the thigh and a second anchor part is fastened around the lower leg.

DESCRIPTION OF EMBODIMENTS

First Embodiment of the Present Invention

Figure 1:
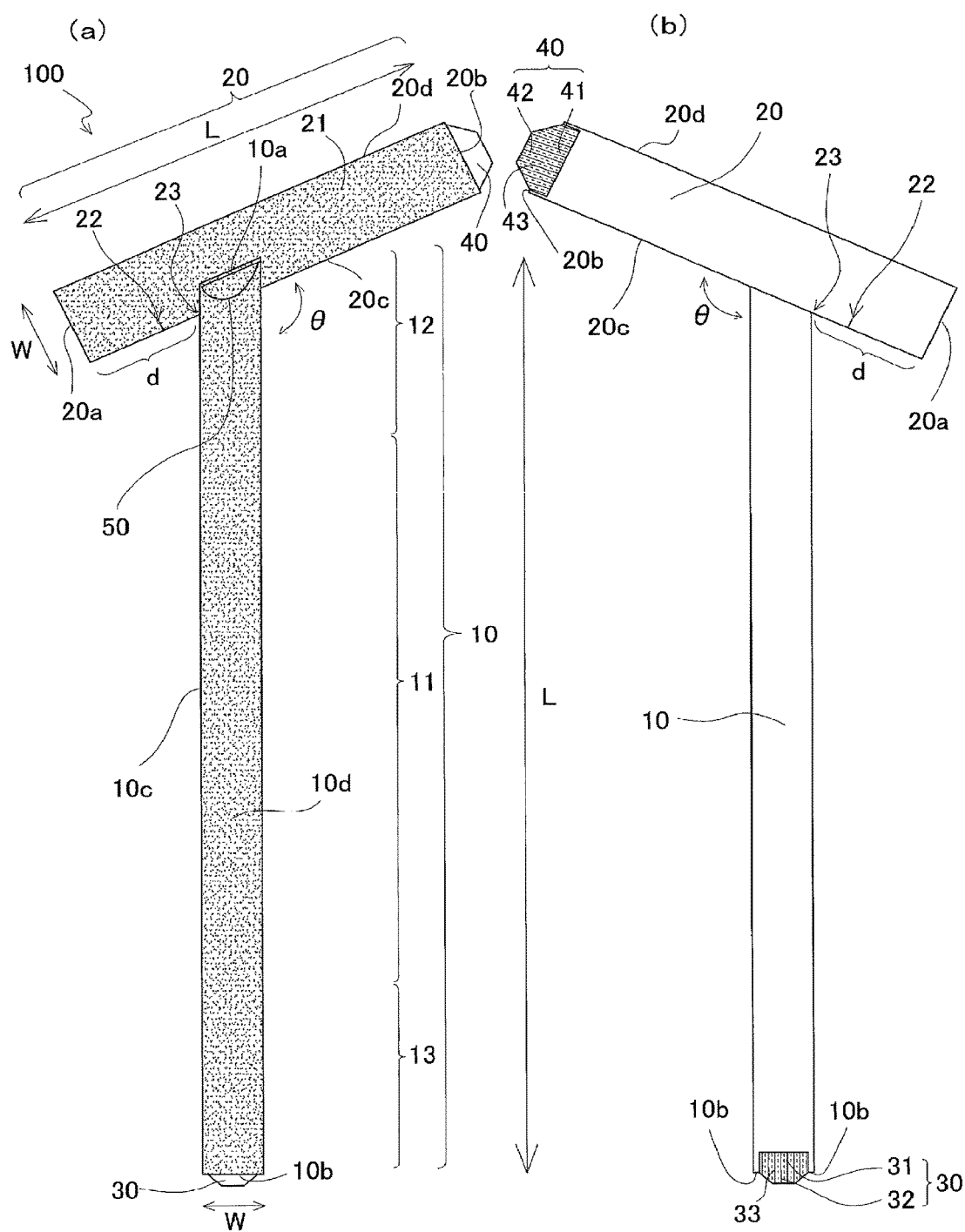
FIG. 1(a) is a front view showing a schematic configuration of a knee joint bandage according to a first embodiment.
FIG. 1(b) is a back view of the knee joint bandage shown in FIG. 1(a).

In the present invention, a bandage means a "thing which includes a band-shaped fabric having stretchability in a warp direction as a main material and in which the band-shaped fabric is wound around a part of the body, thereby being able to assist a function of the body", and as long as it has such an effect, even if it is not expressed as a bandage (for example, a taping supporter, a supporter band, or the like), it is within the scope of the bandage according to the present invention.

A knee joint bandage 100 according to the present invention comprises: a main body part 10 which is woven in a fabric having a loop face 10d of a touch fastener and is composed of a winding part 11 which is wound around the lower leg of a wearer, a first supporting part 12 which is disposed in a taut state on one side of a part corresponding to the patella of the wearer, and a second supporting part 13 which is disposed in a taut state on the other side of the part corresponding to the patella of the wearer to cross the first supporting part 12 below the part corresponding to the patella of the wearer; a first anchor part 20 which is joined to one end 10a of the main body part 10, is woven in a fabric having a loop face 21 of a touch fastener, and is fastened around the thigh of the wearer; and a first engaging part 30 which is joined to the other end 10b of the main body part 10 and has a hook face 33 of a touch fastener, which is detachably stuck to the loop face 21 of the first anchor part 20, as shown in FIGS. 1 to 9. In addition, the knee joint bandage 100 has a double use for both the right knee and left knee in which it can be worn on the knee of either of the right foot or the left foot of the wearer.

The first anchor part 20 is fastened around the thigh of a wearer, thereby positioning the knee joint bandage 100 with respect to the knee joint of the wearer, and serves as an upper anchor of the main body part 10 crossing below the knee of the wearer.

Each of the main body part 10 and the first anchor part 20 has a band shape and is made of a narrow stretchable fabric which is woven in combination of a warp 1 and a weft 2 by a power loom such as a needle loom or a jacquard needle loom, has stretchability in a warp direction (a longitudinal direction L or a circumferential direction), and is inhibited in stretchability in a weft direction (a width direction W).

Further, the main body part 10 is composed of the winding part 11 which is wound around the lower leg of a wearer, the first supporting part 12 which is disposed in a taut state on one side of the part corresponding to the patella of the wearer, and the second supporting part 13 which is disposed in a taut state on the other side of the part corresponding to the patella of the wearer to cross the first supporting part 12 below the part corresponding to the patella of the wearer, in which the first supporting part 12 is provided on the one end 10a side of the main body part 10, the second supporting part 13 is provided on the other end 10b side of the main body part 10, the winding part 11 is provided between the first supporting part 12 and the second supporting part 13, and the first supporting part 12, the winding part 11, and the second supporting part 13 have straight line shapes having the same width.

Figure 6:
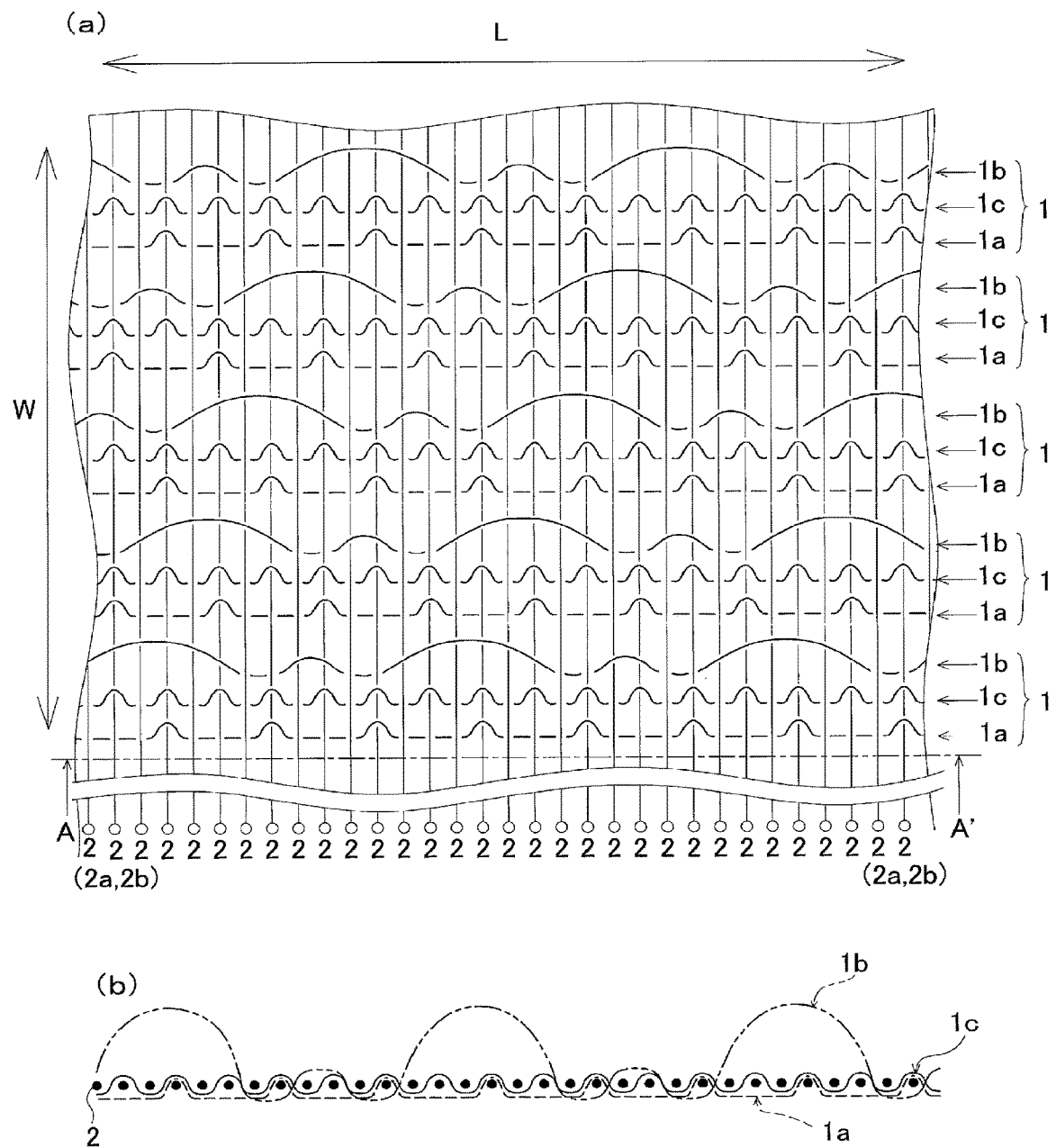
FIG. 6(a) is an explanatory diagram for describing an example of a fabric weave of a loop face of the main body part shown in FIG. 1.
FIG. 6(b) is a cross-sectional view taken along line A-A' and viewed in the direction of an arrow, of the fabric weave shown in FIG. 6(a).

Further, the warp 1 of each of the main body part 10 and the first anchor part 20 is provided with a warp ground yarn 1a which configures one face (for example, a back ground face) of a fabric along with the weft 2, a pile yarn 1b which forms loops on the other face (for example, a front ground face) of the fabric by floating on a plurality of wefts 2 adjacent to each other in the warp direction, and an elastic yarn 1c which provides stretchability in the warp direction, as shown in FIG. 6. Hereinafter, in this specification, each of a face having the loop face 10d of the main body part 10 and a face having the loop face 21 of the first anchor part 20 is referred to as a "front ground face", and a back face thereof is referred to as a "back ground face".

The weft 2 is provided with a weft ground yarn 2a which configures the back ground face of the fabric along with the warp ground yarn 1a, and a fusion yarn 2b which is provided parallel to the weft ground yarn 2a and has thermal adhesiveness, and a single piece of weft ground yarn 2a and a single piece of fusion yarn 2b are provided in parallel, thereby configuring a single piece of weft 2. Further, in FIGS. 6 and 7, a single piece of weft ground yarn 2a and a single piece of fusion yarn 2b are shown as a single piece of weft 2. Further, in FIGS. 6(b) and 7(b), on the basis of the wefts 2 which are provided in parallel, the upper side is the front ground face and the lower side is the back ground face.

Figure 2:
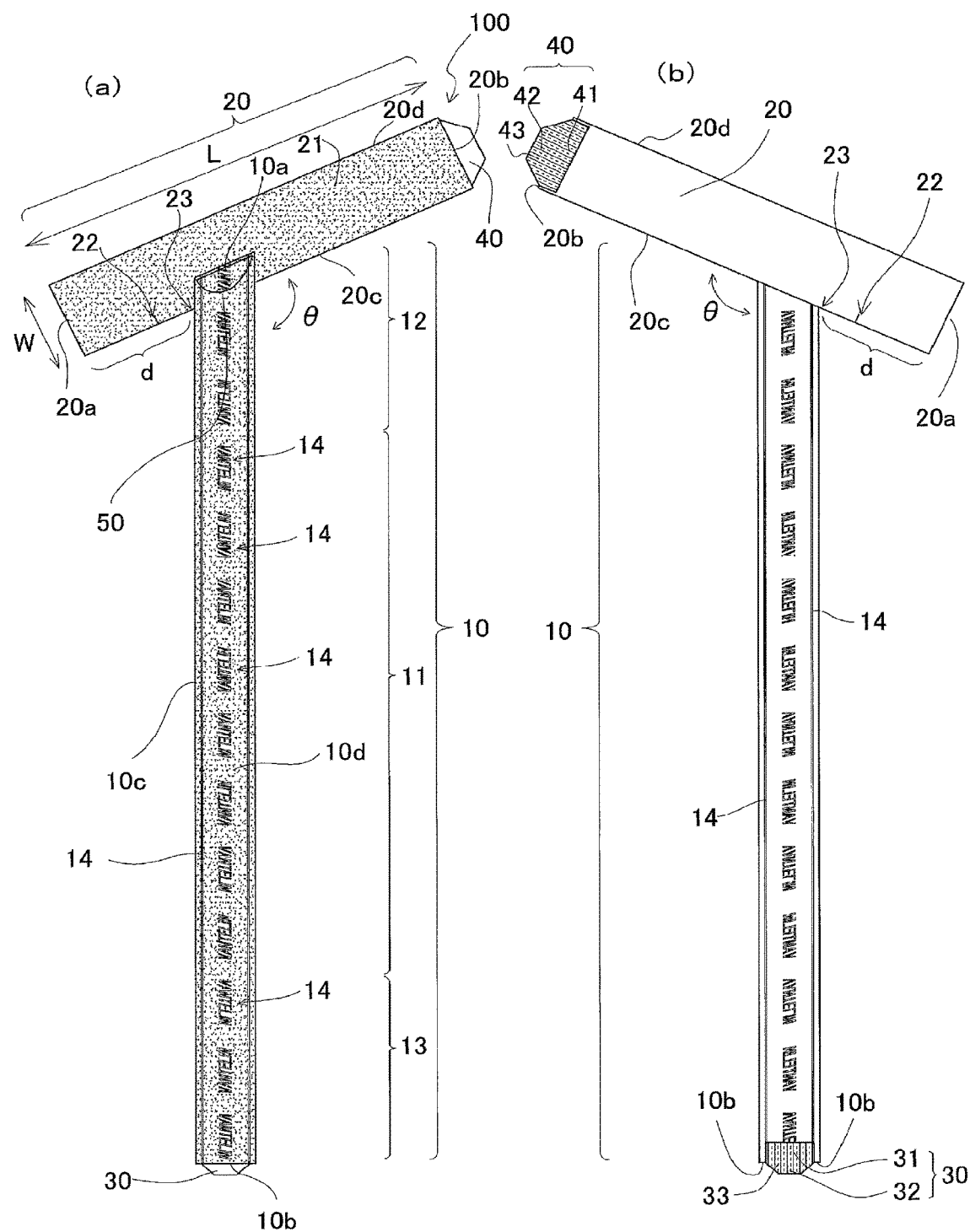
FIG. 2(a) is a front view showing a schematic configuration of a knee joint bandage in which a pattern is formed in a main body part shown in FIG. 1.
FIG. 2(b) is a back view of the knee joint bandage shown in FIG. 2(a).

Further, in the main body part 10, a pattern 14 composed of characters, figures, symbols, or a combination thereof can be partially formed in the front ground face in a jacquard weave which is freely opened, as shown in FIG. 2, by making the warp ground yarn 1a of the warp 1 float to the front ground face side and making the pile yarn 1b of the warp 1 sink to the back ground face, with respect to the plurality of wefts 2 adjacent to each other in the warp direction (the longitudinal direction L), by using a jacquard needle loom, and the main body part 10 has loops (the loop face 10d) on substantially the entire surface of the front ground face with the exception of the regions of the patterns 14.

Further, the first anchor part 20 according to this embodiment is woven by a needle loom because the pattern 14 is not formed therein.

Next, an example of a fabric weave of each of the main body part 10 and the first anchor part 20 according to this embodiment will be described by using FIG. 6. That is, the warp ground yarn 1a forming the loop face 10d (the loop face 21) configures a fabric weave by repeating 1-3 float-sink with respect to the weft 2 (the weft ground yarn 2a and the fusion yarn 2b), in which the warp ground yarn 1a floats so as to pass on the upper side with respect to a single piece of weft 2 (weft ground yarn 2a and fusion yarn 2b) and sinks so as to pass on the lower side with respect to three pieces of wefts 2 (weft ground yarns 2a and fusion yarns 2b) adjacent to each other, as shown in FIG. 6(b).

Further, the pile yarn 1b forming the loop face 10d (the loop face 21) configures a fabric weave by repeating 6-2-2-2 float-sink with respect to the weft 2 (the weft ground yarn 2a and the fusion yarn 2b), in which the pile yarn 1b floats so as to pass on the upper side with respect to six pieces of wefts 2 (weft ground yarns 2a and fusion yarns 2b) adjacent to each other, sinks so as to pass on the lower side with respect to two pieces of wefts 2 (weft ground yarns 2a and fusion yarns 2b) adjacent to each other, floats so as to pass on the upper side with respect to two pieces of wefts 2 (weft ground yarns 2a and fusion yarns 2b) adjacent to each other, and sinks so as to pass on the lower side with respect to two pieces of wefts 2 (weft ground yarns 2a and fusion yarns 2b) adjacent to each other, as shown in FIG. 6(*b*).

Further, the elastic yarn 1c forming the loop face 10d (the loop face 21) configures a fabric weave by repeating 1-1 float-sink with respect to the weft 2 (the weft ground yarn 2a and the fusion yarn 2b), in which the elastic yarn 1c floats so as to pass on the upper side with respect to a single piece of weft 2 (weft ground yarn 2a and fusion yarn 2b) and sinks so as to pass on the lower side with respect to a single piece of weft 2 (weft ground yarn 2a and fusion yarn 2b), as shown in FIG. 6(*b*).

In addition, the fabric weave composed of the warp ground yarn 1a, the pile yarn 1b, and the elastic yarn 1c shown in FIG. 6 is an example, and as long as it is possible to have loops (the loop face 10d or the loop face 21) on the front ground face, there is no limitation to this fabric weave.

Subsequently, an example of a fabric weave of the pattern 14 which is formed in the main body part 10 according to this embodiment will be described by using FIG. 7. That is, the warp ground yarn 1a forming the pattern 14 configures a fabric weave by repeating 3-1 float-sink with respect to the weft 2 (the weft ground yarn 2a and the fusion yarn 2b), in which the warp ground yarn 1a floats so as to pass on the upper side with respect to three pieces of wefts 2 (weft ground yarns 2a and fusion yarns 2b) adjacent to each other and sinks so as to pass on the lower side with respect to a single piece of weft 2 (weft ground yarn 2a and fusion yarn 2b), as shown in FIG. 7(*b*).

Figure 7:
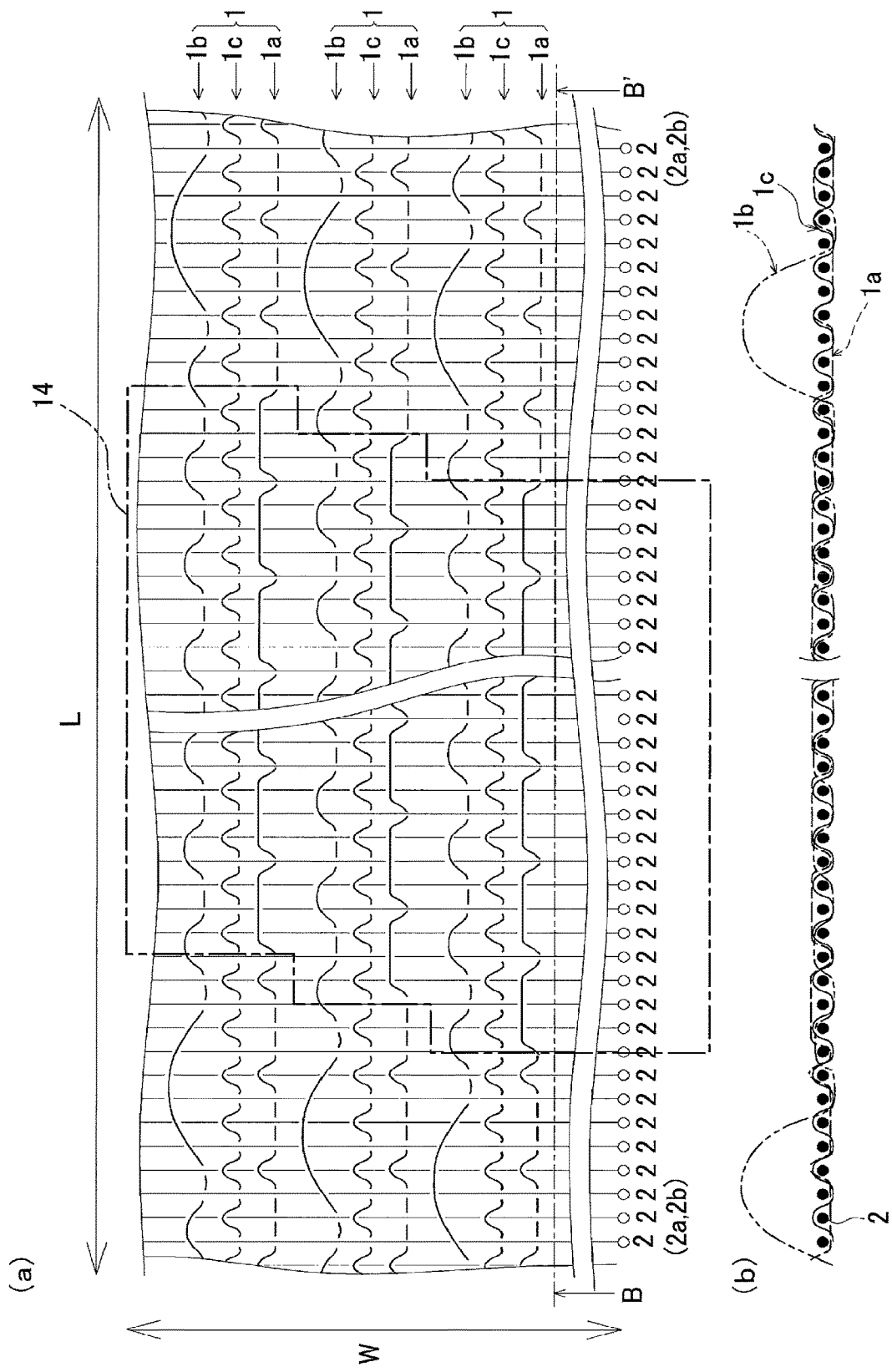
FIG. 7(a) is an explanatory diagram for describing an example of a fabric weave in a loop face and a pattern part of the main body part shown in FIG. 2.
FIG. 7(b) is a cross-sectional view taken along line B-B' and viewed in the direction of an arrow, of the fabric weave shown in FIG. 7(a).

Further, the pile yarn 1b forming the pattern 14 configures a fabric weave by repeating 2-2 float-sink with respect to the weft 2 (the weft ground yarn 2a and the fusion yarn 2b), in which the pile yarn 1b sinks so as to pass on the lower side with respect to two pieces of wefts 2 (weft ground yarns 2a and fusion yarns 2b) adjacent to each other and floats so as to pass on the upper side with respect to two pieces of wefts 2 (weft ground yarns 2a and fusion yarns 2b) adjacent to each other, as shown in FIG. 7(*b*).

Further, the elastic yarn 1c forming the pattern 14 configures a fabric weave by repeating 1-1 float-sink with respect to the weft 2 (the weft ground yarn 2a and the fusion yarn 2b), in which the elastic yarn 1c floats so as to pass on the upper side with respect to a single piece of weft 2 (weft ground yarn 2a and fusion yarn 2b) and sinks so as to pass on the lower side with respect to a single piece of weft 2 (weft ground yarn 2a and fusion yarn 2b), as shown in FIG. 7(*b*).

In addition, the fabric weave composed of the warp ground yarn 1a, the pile yarn 1b, and the elastic yarn 1c shown in FIG. 7 is an example, and as long as it is possible to form the pattern 14 in the loop face 10d of the front ground face, there is no limitation to this fabric weave.

Further, in each of the main body part 10 and the first anchor part 20, it is possible to freely adjust the maximum elongation in the warp direction (the longitudinal direction L) by the quality of the materials of the warp 1 and the weft 2 (in particular, the thicknesses of the elastic yarn 1c and the weft ground yarn 2a) and the number of times of picking (the number) of the weft 2. In the present invention, the maximum elongation refers to the "percentage of the difference between the longest length (an elongation dimension) when having been stretched with the highest load and the original length (a lay-flat size) with respect to the original length".

In particular, from the results of the overall determination of a sensory evaluation which will be described later, it is preferable that the maximum elongation in the warp direction (the longitudinal direction L) of the main body part 10 according to this embodiment is set to be in a range of 40% to 80%, and a range of 45% to 75% is more preferable, and the most preferred is 60%.

Further, it is preferable that the maximum elongation in the warp direction (the longitudinal direction L) of the first anchor part 20 according to this embodiment is greater than the maximum elongation in the warp direction (the longitudinal direction L) of the main body part 10.

In this manner, in the knee joint bandage 100, the maximum elongation in the warp direction (the longitudinal direction L) of the first anchor part 20 is greater than the maximum elongation in the warp direction (the longitudinal direction L) of the main body part 10, whereby it is possible to reduce a burden on the knee joint by improving the stability of the knee joint by fixing the knee joint by a tightening force of the main body part 10 while suppressing a fastening force of the first anchor part 20 on the thigh of a wearer (without causing a feeling of discomfort of the wearer due to constriction of a blood flow of the thigh).

Here, an embodiment in which the maximum elongation of the main body part 10 is set to be 60% and the maximum elongation of the first anchor part 20 is set to be 80% will be described. With respect to the warp ground yarn 1a of the main body part 10 according to this embodiment, a woolly nylon two-fold yarn having a thickness of 100 counts is preferable, and in the main body part 10 according to this embodiment, it is preferable to use 132 pieces of woolly nylon two-fold yarns.

Further, with respect to the warp ground yarn 1a of the first anchor part 20 according to this embodiment, a woolly nylon two-fold yarn having a thickness of 100 counts is preferable, and in the first anchor part 20 according to this embodiment, it is preferable to use 200 pieces of woolly nylon two-fold yarns.

Further, the pile yarn 1b of the main body part 10 according to this embodiment is a special textured yarn (210D-10F) obtained by twisting 10 pieces of nylon filaments together, then applying heat thereto, and further performing twisting in a direction opposite to the twisting direction of the 10 pieces of nylon filaments, and having a thickness of 210 deniers, and in the main body part 10 according to this embodiment, it is preferable to use 132 pieces of special textured yarns (210D-10F).

Further, the pile yarn 1b of the first anchor part 20 according to this embodiment is a special textured yarn (210D-10F) obtained by twisting 10 pieces of nylon filaments together, then applying heat thereto, and further performing twisting in a direction opposite to the twisting direction of the 10 pieces of nylon filaments, and having a thickness of 210 deniers, and in the first anchor part 20 according to this embodiment, it is preferable to use 200 pieces of special textured yarns (210D-10F).

Further, with respect to the elastic yarn 1c of the main body part 10 according to this embodiment, a polyurethane yarn having a thickness of 560 deniers is preferable, and in the main body part 10 according to this embodiment, it is preferable to use 36 pieces of polyurethane yarns.

Further, with respect to the elastic yarn 1c of the first anchor part 20 according to this embodiment, a polyurethane yarn having a thickness of 840 deniers is preferable, and in the first anchor part 20 according to this embodiment, 53 pieces of polyurethane yarns are used.

That is, in the main body part 10 according to this embodiment, for example, if a width is 5 cm, warp density by the warps 1 (the warp ground yarns 1a, the pile yarns 1b, and the elastic yarns 1c) is 1485.6D/mm(=((210D×132 pieces)+(100D×2 pieces×132 pieces)+(560D×36 pieces))/50 mm).

Further, in the first anchor part 20 according to this embodiment, for example, if a width is 8 cm, warp density by the warps 1 (the warp ground yarns 1a, the pile yarns 1b, and the elastic yarns 1c) is 1581.5D/mm(=((210D×200 pieces)+(100D×2 pieces×200 pieces)+(840D×53 pieces))/80 mm).

Further, in the pile yarn 1b of each of the main body part 10 and the first anchor part 20 according to this embodiment, a filament count is 10 pieces, whereby there is an advantage that, compared to a case where a filament count is a low count (for example, 7 pieces), an adhesive force between dense filaments is high and a feel of the fabric (each of the main body part 10 and the first anchor part 20) is soft.

Further, the elastic yarn 1c of the main body part 10 according to this embodiment has a thickness of 560 deniers, thereby making the thickness of the fabric (the main body part 10) thin, compared to the case of a thick elastic yarn (for example, 1120 deniers), and thus it is possible to soften the fabric itself.

Further, with respect to the weft ground yarn 2a of the main body part 10 according to this embodiment, it is preferable to use a single piece of polyester woolly yarn (EW) having a thickness of 150 deniers.

Further, with respect to the fusion yarn 2b of the main body part 10 according to this embodiment, it is preferable to use a single piece of nylon thermal fusion yarn (for example, "Elder (registered trademark)" manufactured by Toray Industries, Inc.) having a thickness of 100 deniers.

Further, in the main body part 10 according to this embodiment, a single piece of weft ground yarn 2a and a single piece of fusion yarn 2b are simultaneously picked as the weft 2 by a power loom, and the number of times of picking (the number) of the weft 2 (the weft ground yarn 2a and the fusion yarn 2b) is 36.9 times (each 36.9 pieces) per 2.54 cm (1 inch).

Further, with respect to the weft ground yarn 2a of the first anchor part 20 according to this embodiment, it is preferable to use a single piece of polyester woolly yarn (EW) having a thickness of 150 deniers.

Further, with respect to the fusion yarn 2b of the first anchor part 20 according to this embodiment, it is preferable to use a single piece of nylon thermal fusion yarn (for example, "Elder (registered trademark)" manufactured by Toray Industries, Inc.) having a thickness of 100 deniers.

Further, in the first anchor part 20 according to this embodiment, a single piece of weft ground yarn 2a and a single piece of fusion yarn 2b are simultaneously picked as the weft 2 by a power loom, and the number of times of picking (the number) of the weft 2 (the weft ground yarn 2a and the fusion yarn 2b) is 30.8 times (each 30.8 pieces) per 2.54 cm (1 inch).

That is, in the main body part 10 in the quality of material and the number of times of picking (the number) of the weft 2 described above, weft density by the wefts 2 (the polyester woolly yarns and the nylon thermal fusion yarns) is 9225D/inch(=(150D+100D)×36.9 times/inch).

Further, in the first anchor part 20 in the quality of material and the number of times of picking (the number) of the weft 2 described above, weft density by the wefts 2 (the polyester woolly yarns and the nylon thermal fusion yarns) is 7700D/inch(=(150D+100D)×30.8 times/inch).

Further, the weft ground yarn 2a of the weft 2 of each of the main body part 10 and the first anchor part 20 according to this embodiment has a thickness of 150 deniers, whereby it is possible to make the thickness of the fabric (each of the main body part 10 and the first anchor part 20) thin, compared to the case of a weft ground yarn (for example, 300 deniers) which is a thick weft.

In this manner, in the main body part 10 according to this embodiment, due to the quality of the materials of the warp 1 and the weft 2 (in particular, the thicknesses of the elastic yarn 1c and the weft ground yarn 2a) described above and the number of times of picking (the number) of the weft 2 described above, it is possible to set the maximum elongation in the warp direction (the longitudinal direction L) to be 60%.

Further, in the first anchor part 20 according to this embodiment, due to the quality of the materials of the warp 1 and the weft 2 (in particular, the thicknesses of the elastic yarn 1c and the weft ground yarn 2a) described above and the number of times of picking (the number) of the weft 2 described above, it is possible to set the maximum elongation in the warp direction (the longitudinal direction L) to be 80%.

Further, with respect to the thickness of the elastic yarn 1c according to this embodiment, 560 deniers has been given as an example. However, in the present invention, available (mass-producible) 420 deniers which is a thickness lower by 1 rank, or 1120 deniers which is a thickness higher by 1 rank may be selected, and the thickness and the number of times of picking (the number) of the weft 2 described above may be changed. That is, if the thickness of the elastic yarn 1c according to this embodiment is in a range of 420 deniers to 1120 deniers, it is possible to set the maximum elongation in the warp direction of the main body part 10 to be the maximum elongation within the above-described range. Further, it is also possible to set the maximum elongation in the warp direction of the first anchor part 20 to be the maximum elongation within a desired range.

Further, with respect to the thickness of the weft ground yarn 2a of the weft 2 according to this embodiment, 150 deniers has been given as an example. However, in the present invention, available (mass-producible) 100 deniers which is a thickness lower by 1 rank, or 300 deniers which is a thickness higher by 1 rank may be selected, and the thickness of the elastic yarn 1c and the number of times of picking (the number) of the weft 2 described above may be changed. That is, if the thickness of the weft ground yarn 2a of the weft 2 according to this embodiment is in a range of 100 deniers to 300 deniers, it is possible to set the maximum elongation in the warp direction of the main body part 10 to be the maximum elongation within the above-described range. Further, it is also possible to set the maximum elongation in the warp direction of the first anchor part 20 to be the maximum elongation within a desired range.

Further, with respect to the number of times of picking (the number) of the weft 2 (the weft ground yarn 2a and the fusion yarn 2b) according to this embodiment, 36.9 times (each 36.9 pieces) per 2.54 cm (1 inch) has been given as an example. However, in the present invention, the number of times of picking (the number) of the weft 2 (the weft ground yarn 2a and the fusion yarn 2b) in a range of 32.8 times (each 32.8 pieces) per 2.54 cm to 41.0 times (each 41.0 pieces) per 2.54 cm may be selected, and the thicknesses of the elastic yarn 1c and the weft 2 described above may be changed. That is, if the number of times of picking (the number) of the weft 2 (the weft ground yarn 2a and the fusion yarn 2b) according to this embodiment is in a range of 32.8 times (each 32.8 pieces) per 2.54 cm to 41.0 times (each 41.0 pieces) per 2.54 cm, it is possible to set the maximum elongation in the warp direction of the main body part 10 to be the maximum elongation within the above-described range. Further, it is also possible to set the maximum elongation in the warp direction of the first anchor part 20 to be the maximum elongation within a desired range.

Further, in a case where the thickness of the main body part 10 is too thick, when winding the bandage around the lower leg of a wearer, it becomes bulky, and thus it becomes difficult to wind it, and in a case where the thickness of the main body part 10 is too thin, the fabric itself of the bandage is easily foldable, and thus a desired fixing force is not obtained. For this reason, it is preferable that the thickness of the main body part 10 is set to be a thickness in which it is easy to wind the bandage and a desired fixing force is obtained, and for example, if the maximum elongation in the warp direction (the longitudinal direction L) of the main body part 10 is 60%, it is preferable to set the thickness of the main body part 10 to be less than or equal to 3 mm.

Further, in a case where the thickness of the first anchor part 20 is too thick, when fastening the first anchor part 20 around the thigh of a wearer, it becomes bulky, and thus it becomes difficult to wind it, and in a case where the thickness of the first anchor part 20 is too thin, the fabric itself of the bandage is easily foldable, and thus a desired fastening force is not obtained. For this reason, it is preferable that the thickness of the first anchor part 20 is set to be a thickness in which it is easy to fasten the first anchor part 20 around the thigh of a wearer and a desired fastening force is obtained, and if the maximum elongation in the warp direction (the longitudinal direction L) of the first anchor part 20 is 80%, it is preferable to set the thickness of the first anchor part 20 to be less than or equal to 4 mm.

Further, in the first anchor part 20 according to this embodiment, the loops (the loop face 21) are provided on a face (the front ground face) which becomes the outside in a case where the first anchor part 20 is fastened around the thigh of a wearer, and therefore, a second engaging part 40 (a hook face 43) provided at the first anchor part 20 is provided on the back ground face side of one end 20a or the other end 20b of the first anchor part 20 in terms of the ease of attachment and detachment and the degree of freedom of an engaging position.

Similarly, the first engaging part 30 (the hook face 33) provided at the main body part 10 is provided on the back ground face side of the other end 10b of the main body part 10 in terms of the ease of attachment and detachment and the degree of freedom of an engaging position.

Further, in the main body part 10, in order to configure a crossing portion below the knee and a lower anchor, the lengths of portions (the first supporting part 12 and the second supporting part 13) which cross each other below the knee of a wearer, and the length of a portion (the winding part 11) which circles around the lower leg of the wearer at least once are required, and although there is an individual difference in the circumference of the knee or the thickness of the lower leg according to gender, age, or the like, it is conceivable that the length of the main body part 10 is set to in a range of 68 cm to 88 cm, for example. Further, in the main body part 10, a certain level of width is required in order to effectively perform the fixing of the knee joint of the wearer, and it is preferable to set the width to be 5 cm, for example.

Further, the main body part 10 according to this embodiment is woven in a fabric having the loop face 10d of a touch fastener. However, if the maximum elongation in the warp direction (the longitudinal direction L) is a desired maximum elongation, the loop face 10d of a touch fastener is not necessarily required.

However, the main body part 10 is woven in a fabric having the loop face 10d of a touch fastener, whereby compared to a case where it does not have the loop face 10d, when being in non-use, it is possible to compactly store the knee joint bandage 100 by rolling it and making the hook face 33 of the first engaging part 30 be engaged with the loop face 10d of the main body part 10, and depending on a wearer, there is also a case of using the knee joint bandage 100 with the hook face 33 of the first engaging part 30 be engaged with the main body part 10, and thus a degree of freedom can be provided in a use method (an engaging position) of the knee joint bandage 100.

Furthermore, in the first anchor part 20 according to this embodiment, the second engaging part 40 having the hook face 43 of a touch fastener, which is detachably stuck to the loop face 21 of the first anchor part 20, is provided on the back ground face side of one end 20a or the other end 20b (in FIG. 1, the other end 20b), whereby the adjustment of the circumferential length of the first anchor part 20 becomes simple, and thus it is possible to cope with the thicknesses of the thighs of various wearers. Further, the first anchor part 20 may be formed in a ring shape by sewing one end 20a and the other end 20b to each other in a circumferential length in which it is possible to fasten the first anchor part 20 around the thigh of a wearer.

Further, in the first anchor part 20 according to this embodiment, in order to circle around the thigh of a wearer, it is preferable that, for example, the length of a band-shaped body is set in a range of 34 cm to 38 cm.

Further, if the fastening forces on the thigh and the lower leg of a wearer by the first anchor part 20 and the main body part 10 (the winding part 11) are too strong, constriction of a blood flow occurs in the thigh and the lower leg, causing a feeling of discomfort to the wearer. In particular, the feeling of discomfort is remarkable in the thigh, compared to the lower leg.

For this reason, in the knee joint bandage 100 according to this embodiment, a feeling of discomfort to a wearer is alleviated by dispersing pressure, which is applied to the body surface of the wearer by the first anchor part 20, by widening the area of the first anchor part 20 which comes into contact with the body surface, relative to the main body part 10 (the winding part 11).

That is, it is preferable that the width of the first anchor part 20 according to this embodiment is set to be wider than the width of the main body part 10 and be in a range of 6 cm to 8 cm, for example.

Further, the first anchor part 20 and the main body part 10 according to this embodiment are joined to each other with an angle θ between the longitudinal direction L of the first anchor part 20 and the longitudinal direction L of the main body part 10 being 120°, as shown in FIG. 1. However, if the main body part 10 can cross below the knee in a case where the knee joint bandage 100 has been worn, there is no limitation to the above angle θ.

Further, in a case of pulling the main body part 10 from one end 10a to the other end 10b side, the closer the angle θ is to 180°, the more a force acts in the longitudinal direction L of the first anchor part 20, whereby the first anchor part 20 rotates, and the closer the angle θ is to 90°, the more a force acts in the width direction W of the first anchor part 20, whereby the first anchor part 20 rides up along the lower side of the thigh. For this reason, it is preferable that the range of the angle θ is set to be in a range of 110° to 130° in consideration of the ease of a use method of the knee joint bandage 100 such that in a case of pulling the main body part 10 from one end 10a to the other end 10b side, the main body part 10 can be pulled diagonally downward with respect to the first anchor part 20 in a state where floating does not occur in the first anchor part 20 and the main body part 10 is not twisted in the vicinity of a joining portion 50.

Further, the joining portion 50 between the first anchor part 20 and one end 10a of the main body part 10 is joined at a position where a distance from one end 20a or the other end 20b (in FIG. 1, one end 20a) of the first anchor part 20 corresponds to a length in a range of ¼ to ½ of the length of the first anchor part 20.

In particular, in the knee joint bandage 100 according to this embodiment, as shown in FIG. 1(*a*), in a case where an intersection portion of one side 10c of the main body part 10, which is closer to one end 20a of the first anchor part 20, out of both sides of the main body part 10, with a lower side 20c of the first anchor part 20, which intersects both sides of the main body part 10, out of both sides of the first anchor part 20, is set to be an intersection point 23, a distance (the length of an overlapping portion of the second engaging part 40 and the first anchor part 20) d from one end 20a of the first anchor part 20 to the intersection point 23 in the lower side 20c of the first anchor part 20 is set to be in a range of 6 cm to 11 cm.

In this way, in a case where the knee joint bandage 100 has been worn, an engaging position of the hooks (the hook face 43) of the second engaging part 40 with the loops (the loop face 21) of the first anchor part 20 and an engaging position of the hooks (the hook face 33) of the first engaging part 30 with the loops (the loop face 21) of the first anchor part 20 do not overlap, and thus it is possible to prevent a decrease in engaging force due to overlapping of the hooks (the hook face 33) of the first engaging part 30 and the second engaging part 40.

Further, the joining portion 50 between the first anchor part 20 and one end 10a of the main body part 10 is sewn convexly to the other end 10b side of the main body part 10 so as to become longer than the length in the width direction W of the main body part 10.

In this manner, in the knee joint bandage 100, the joining portion 50 is sewn in a shape convex toward the other end 10b side of the main body part 10, whereby in a case of winding the knee joint bandage 100 around the knee joint of a wearer, a twist at the joining portion 50 can be absorbed in response to the winding (pulling) direction of the main body part 10 and the occurrence of floating or wrinkles in the vicinity of the joining portion 50 can be suppressed.

Further, in a case where the joining portion 50 is formed in a substantially triangular shape, when a wearer wears the knee joint bandage 100, stress is concentrated on the vertex of the triangle due to the tensile stress from the main body part 10, and the cloth of the vertex portion is weakened, and thus there is a concern that the sewn place may collapse.

For this reason, the joining portion 50 according to this embodiment is formed in a substantially semicircular shape, whereby stress does not concentrate even with respect to the tensile stress from the main body part 10, the collapse of the sewn place can be prevented, it is also possible to cope with an individual differences in the pulling direction of the main body part 10, and it is possible to suppress the occurrence of floating or wrinkles in the vicinity of the joining portion 50.

Further, in the joining between the first anchor part 20 and one end 10a of the main body part 10, sewing is not performed on both sides of the main body part 10, whereby both sides of the main body part 10 are not fixed to the first anchor part 20 and the fabrics in both sides in the vicinity of the joining portion 50 of the main body part 10 can be extended.

For this reason, in the knee joint bandage 100 according to this embodiment, even if a winding angle of the main body part 10 with respect to the lower leg of a wearer changes somewhat, distortion of the fabric in each side in the vicinity of the joining portion 50 of the main body part 10 is absorbed, and thus it is possible to suppress the occurrence of floating or wrinkles of the cloth in each side in the vicinity of the joining portion 50 of the main body part 10.

Further, in the knee joint bandage 100 according to this embodiment, as shown in FIG. 1, a center mark 22 by a seam as a mark can be sewn in the vicinity of the joining portion 50 of the first anchor part 20 such that the first anchor part 20 is fastened at a correct position of the thigh of a wearer and a correct winding method on the knee joint of the wearer, in which the main body part 10 crosses below the knee, is obtained.

The first engaging part 30 according to this embodiment has a planar shape of a combination of, for example, a rectangle and an isosceles trapezoid, as shown in FIG. 1(*b*), in which a rectangular portion 31 is sewn to one face (the back ground face) of the main body part 10 and an isosceles trapezoid portion 32 protrudes from the other end 10b of the main body part 10.

Similarly, the second engaging part 40 according to this embodiment has a planar shape of a combination of, for example, a rectangle and an isosceles trapezoid, as shown in FIG. 1(*b*), in which a rectangular portion 41 is sewn to one face (the back ground face) of the first anchor part 20 and an isosceles trapezoid portion 42 protrudes from the other end 20b of the first anchor part 20.

In this manner, in the first engaging part 30 (the second engaging part 40), the isosceles trapezoid portion 32 (the isosceles trapezoid portion 42) protrudes from the other end 10b of the main body part 10 (the other end 20b of the first anchor part 20), thereby becoming thinner by an amount that does not overlap the main body part 10 (the first anchor part 20), whereby it is easy to grip the isosceles trapezoid portion (the isosceles trapezoid portion 42) with the fingers of a wearer, and thus it is possible to easily attach and detach the hook face 33 (the hook face 43) with respect to the loop face 21 of the first anchor part 20.

Next, a method of wearing the knee joint bandage 100 shown in FIGS. 1 and 3 will be described by using FIGS. 4 and 5.

In addition, in the following description, a case of wearing the knee joint bandage 100 on the right knee of a wearer will be described. However, in a case of wearing the knee joint bandage 100 on the left knee of the wearer, wearing is performed with the "right knee", the "outer surface of the lower leg", and the "inner surface of the lower leg" respectively replaced by the "left knee", the "inner surface of the lower leg", and the "outer surface of the lower leg".

Figure 5:
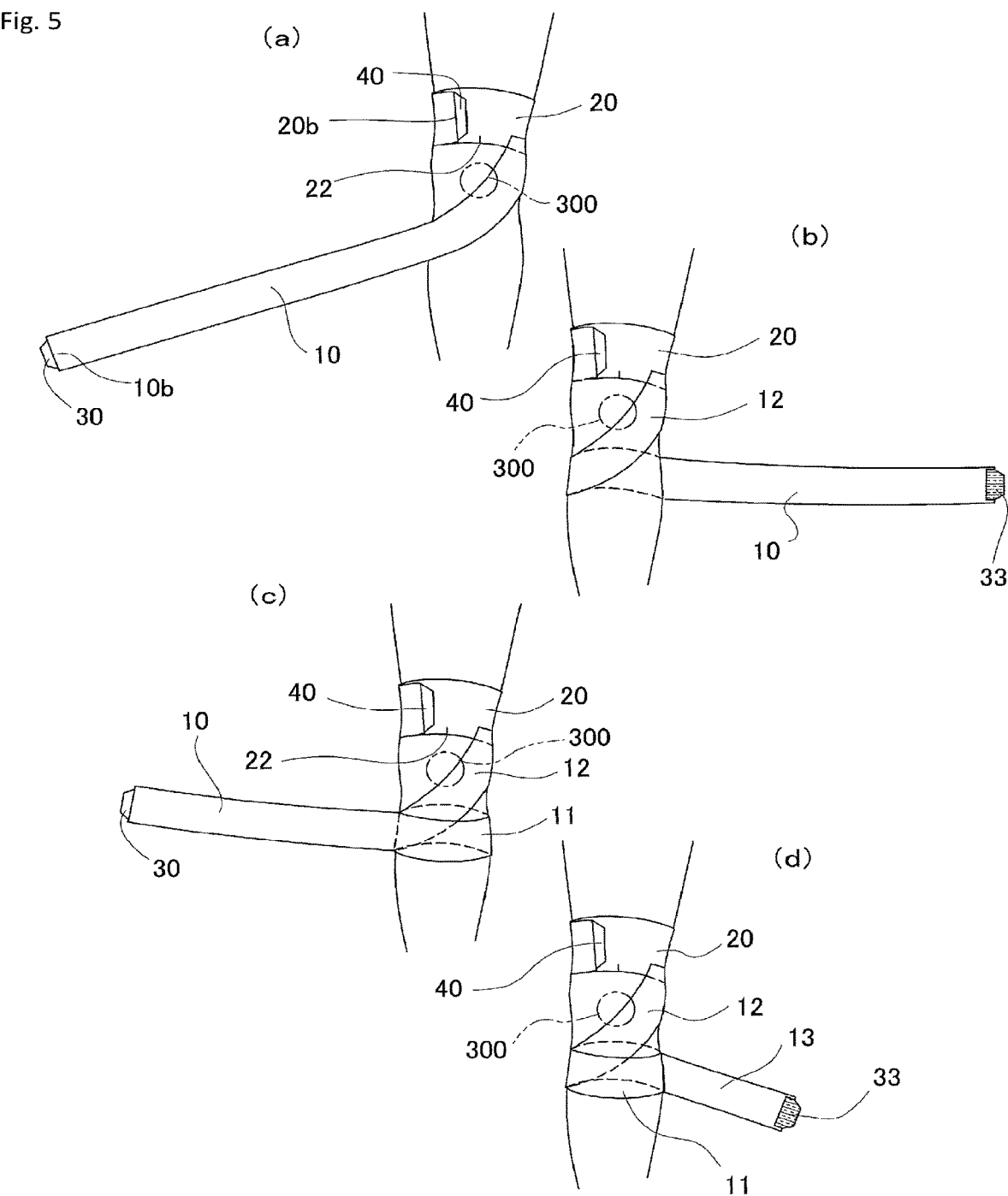
FIG. 5(a) is an explanatory diagram showing a state where an anchor part of the knee joint bandage shown in FIGS. 1 and 3 is fastened around the thigh.
FIG. 5(b) is an explanatory diagram showing a state where a main body part is half-turned below the knee from the outer surface of the lower leg of the right leg.
FIG. 5(c) is an explanatory diagram showing a state where the main body part is further half-turned below the knee from the state shown in FIG. 5(b)
FIG. 5(d) is an explanatory diagram showing a state where the main body part is further half-turned below the knee from the state shown in FIG. 5(c).

A wearer fastens the first anchor part 20 around the thigh by disposing the first anchor part 20 in an extended state at the thigh by winding the first anchor part 20 around the thigh with the right hand while pressing one end 20a of the first anchor part 20 with the left hand with the center mark 22 of the first anchor part 20 fitted to the center of the thigh in the vicinity of the kneecap, and making the hook face 43 of the second engaging part 40 which is located at the other end 20b of the first anchor part 20 be engaged with the loop face 21 of the first anchor part 20, as shown in FIG. 5(*a*). In addition, the extended state refers to a state of having an elongation margin allowing the wearer to finely adjust a winding position after the wearing of the knee joint bandage 100.

Then, the wearer pulls the main body part 10 while gripping the main body part 10 with the right hand and disposes the main body part 10 (the first supporting part 12) in an extended state at the left side of a part corresponding to a patella 300 of the right knee.

Next, the wearer makes the main body part 10 (the winding part 11) in an extended state circle around the lower leg by one round and a half in a direction from the outer surface of the lower leg to the inner surface of the lower leg through a part corresponding to the gastrocnemius by using both hands, as shown in FIGS. 5(b) to 5(d).

Then, the wearer disposes the main body part 10 (the second supporting part 13) in an extended state at the right side of the part corresponding to the patella 300 of the right knee while gripping the other end 10h of the main body part 10 with the right hand.

Finally, the wearer makes the hook face 33 of the first engaging part 30 which is located at the other end 10b of the main body part 10 be engaged with the loop face 21 of the first anchor part 20, as shown in FIG. 4, whereby the wearing is completed.

In addition, in the wearing method of the knee joint bandage 100 described above, a case where in the start of winding of the main body part 10, the main body part 10 (the first supporting part 12) is disposed from the left side of the part corresponding to the patella 300 of the right knee has been described. However, the main body part 10 (the first supporting part 12) may be disposed from the right side of the part corresponding to the patella 300 of the right knee by using the knee joint bandage 100 shown in FIGS. 8 and 9.

Figure 3:
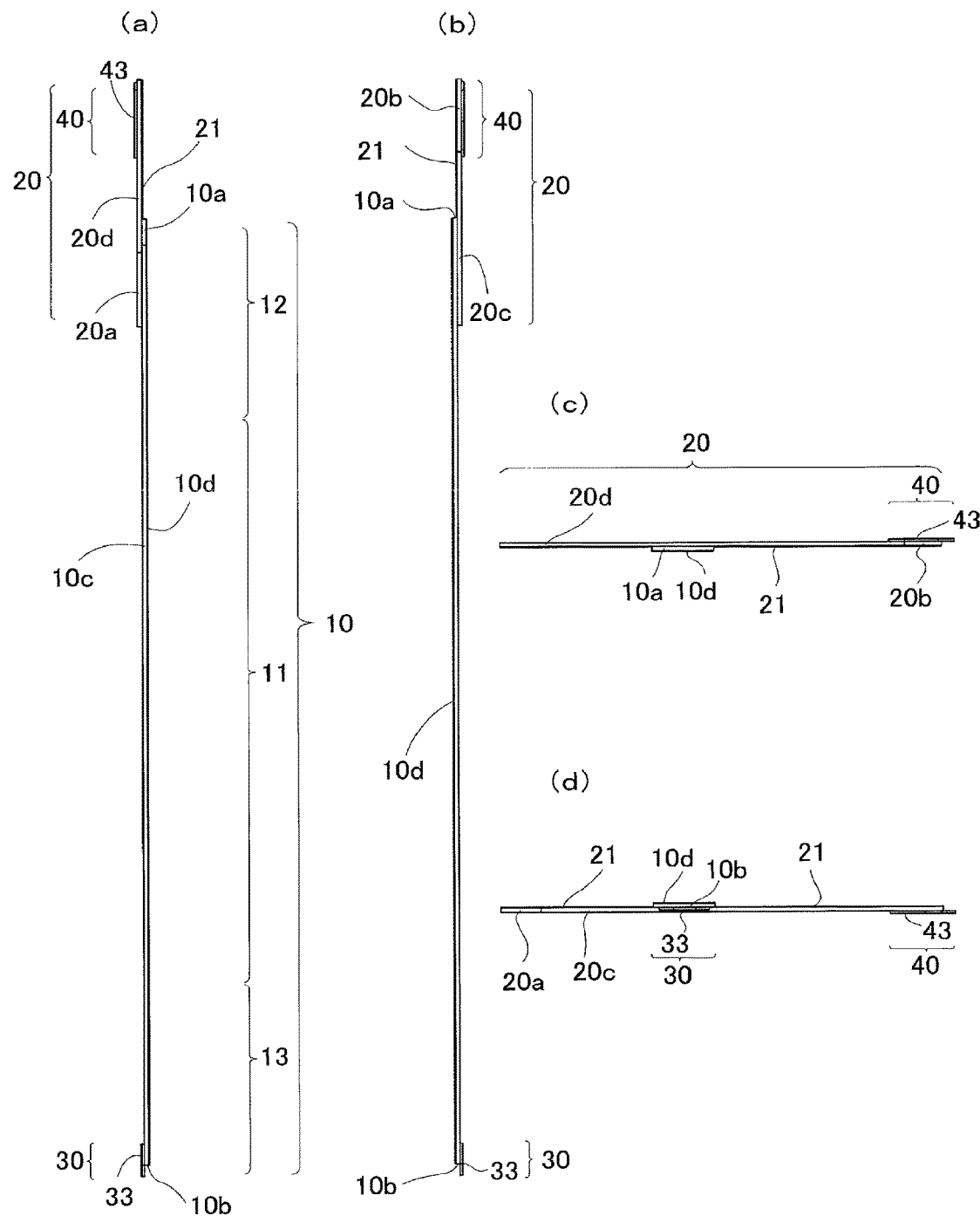
FIG. 3(a) is a left side view of each of the knee joint bandages shown in FIGS. 1(a) and 2(a)
FIG. 3(b) is a right side view of each of the knee joint bandages shown in FIGS. 1(a) and 2(a)
FIG. 3(c) is a plan view of each of the knee joint bandages shown in FIGS. 1(a) and 2(a)
FIG. 3(d) is a bottom view of each of the knee joint bandages shown in FIGS. 1(a) and 2(a).
Figure 8:
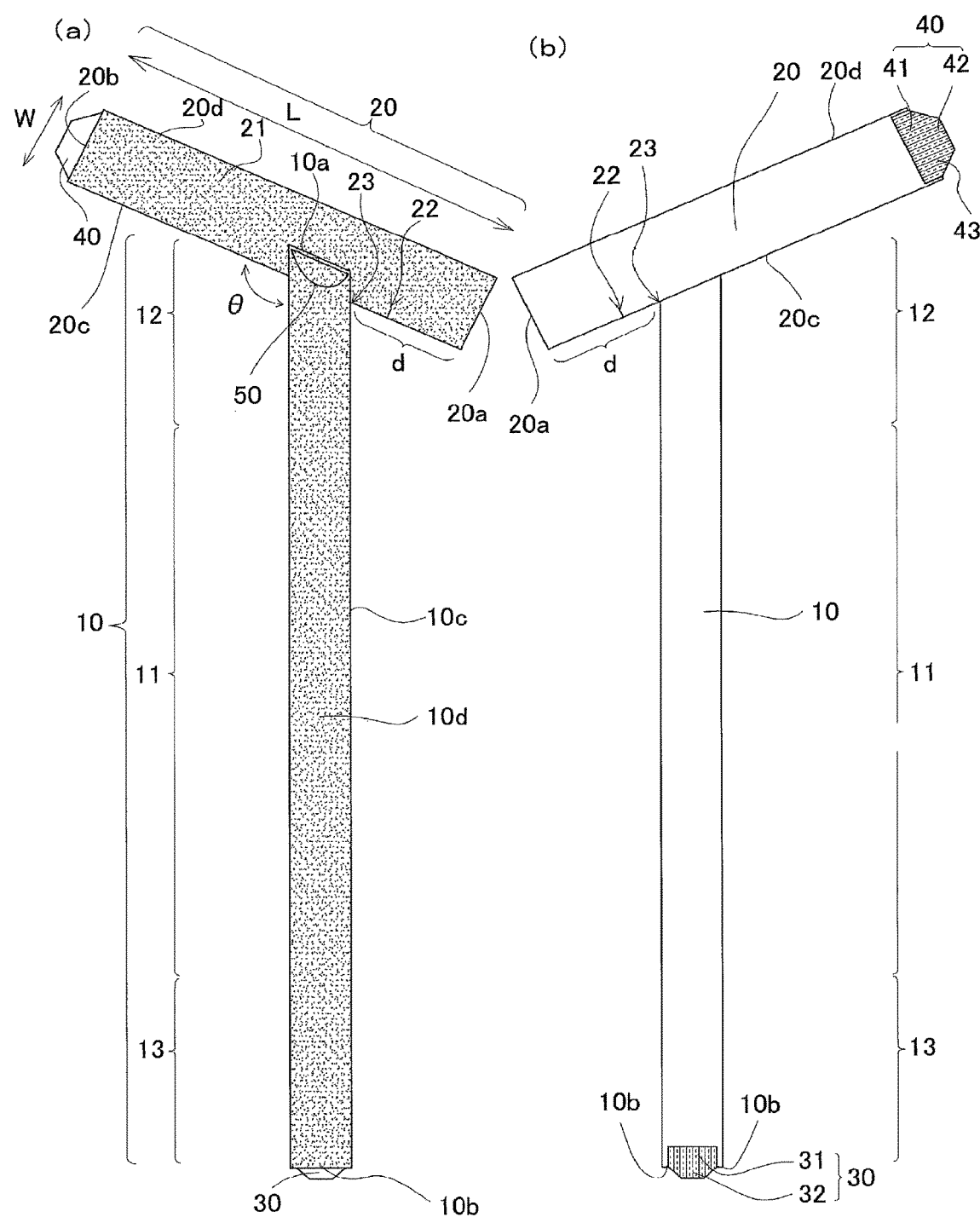
FIG. 8(a) is a front view showing a schematic configuration of another knee joint bandage according to the first embodiment.
FIG. 8(b) is a back view of the knee joint bandage shown in FIG. 8(a).
Figure 9:
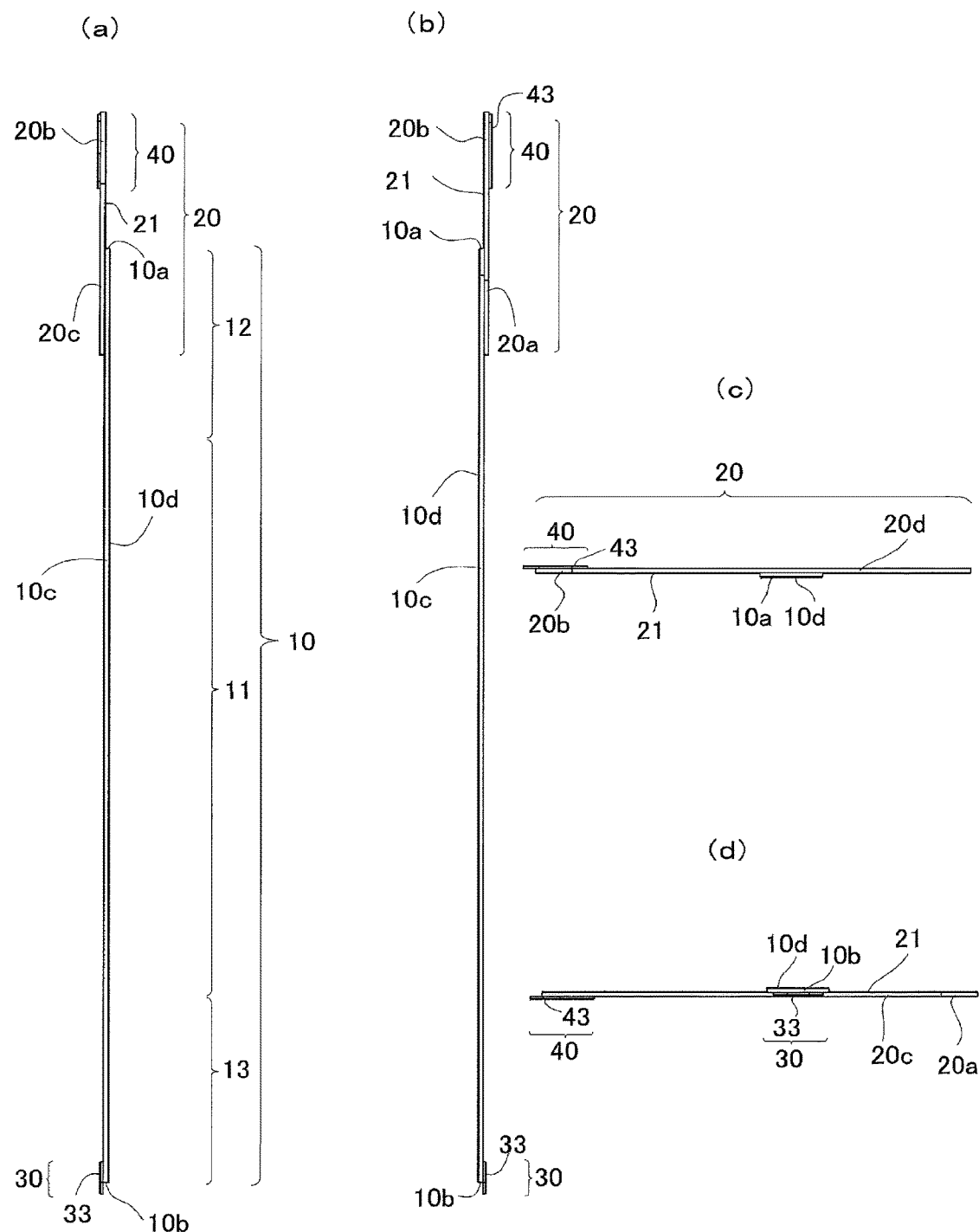
FIG. 9(a) is a left side view of the knee joint bandage shown in FIG. 8(a)
FIG. 9(b) is a right side view of the knee joint bandage shown in FIG. 8(a)
FIG. 9(c) is a plan view of the knee joint bandage shown in FIG. 8(a)
FIG. 9(d) is a bottom view of the knee joint bandage shown in FIG. 8(a).

Further, the knee joint bandage 100 shown in FIGS. 8 and 9 has a structure in which one end 10a of the main body part 10 of the knee joint bandage 100 shown in FIGS. 1 and 3 is joined at a line-symmetric position on the basis of the center mark 22 in the first anchor part 20.

Next, the optimal range of the maximum elongation in the warp direction in the main body part 10 of the knee joint bandage 100 according to this embodiment will be described based on the test results of a trial use test.

In addition, in the trial use test, as shown in FIG. 1, the knee joint bandages 100 (hereinafter, respectively referred to as Example 1, Example 2, and Example 3) each provided with the main body part 10 (length: 80 cm, width: 5 cm) woven with the quality of the materials of the warp 1 and the weft 2 and the number of times of picking (the number) of the weft 2 shown in Table 1 below and having the maximum elongation of 45%, 60%, or 75%, the first anchor part 20, the first engaging part 30, and the second engaging part 40 were fabricated and used.

Further, knee joint bandages (hereinafter, respectively referred to as Comparative Example 1 and Comparative Example 2) were fabricated in the same manner as in the above examples by using the main body part 10 (length: 80 cm, width: 5 cm) having the maximum elongation of 35% or 90% and used in the trial use test.

TABLE 1

| | Quality of material | | | | | Number of times of picking | |
|---|---|---|---|---|---|---|---|
| | Warp | | | Weft | | | |
| | Warp ground yarn | Pile yarn | Elastic yarn | Weft ground yarn | Fusion yarn | (Number) of weft [times/inch] | Maximum elongation [%] |
| Example 1 | WN100/2 | 210D-10F | 560D | EW150D | Elder 100D | 39.8 | 45 |
| Example 2 | WN100/2 | 210D-10F | 560D | EW150D | Elder 100D | 36.9 | 60 |
| Example 3 | WN100/2 | 210D-10F | 560D | EW150D | Elder 100D | 33.8 | 75 |
| Comparative Example 1 | WN100/2 | 210D-10F | 560D | EW150D | Elder 100D | 42.3 | 35 |
| Comparative Example 2 | WN100/2 | 210D-10F | 560D | EW150D | Elder 100D | 30.8 | 90 |

In the trial use test, the knee joint bandage was worn on the right knee of the wearer, as shown in FIG. 4, and the sensory evaluation (a total of five persons) of an effect feeling of the wearer in the evaluation items of FIG. 10 was carried out. In an evaluation method, first, the sensory evaluation for each evaluation item in each wearer was scored in three stages (3: very good, 2: good, and 1: poor), and the average score of all the wearers (5 persons) in each evaluation item was calculated. Thereafter, with respect to Examples 1 to 3 and Comparative Examples 1 and 2, the total points and the average score of each evaluation item were calculated, and comprehensively, the average score of two or more points was determined to be a passing mark.

Further, with respect to the evaluation item "fixing force" of FIG. 10, in a force restraining a range of motion of the knee joint, restraint of the range of motion using a force more than necessary in the flexing action of the knee joint in a movement such as walking, running, or going up and down stairs is supposed. Further, restraint of the range of motion of the flexion of the knee joint in a case of using a force more than necessary in a landing in a jump during sports or a holding-out movement using the knee or a case where a load is applied to the knee is supposed.

Further, with respect to the evaluation item "pain" of FIG. 10, if it is a pain due to a compression force of the fabric, in a case where the maximum elongation of the fabric is small, the fabric cannot follow the movement of a muscle or a joint or the expansion and contraction of the skin, and the compression force is more strongly felt, and thus it is considered that a pain is easily felt, and in a case where the maximum elongation of the fabric is large, it is considered that the fixing force to restrain the range of motion becomes weaker. Further, if it is a rubbing pain due to the hardness of the fabric, in a case where the maximum elongation of the fabric is small, the fabric cannot follow the movement of a muscle or the skin, and therefore, rubbing occurs between the fabric and the skin, and thus it is considered that a pain is easily felt, and in a case where the maximum elongation of the fabric is large, the fabric extends so as to follow a muscle or the skin, and therefore, it is considered that trouble to the skin is less.

Further, with respect to the evaluation item "ease of peeling-off of touch fastener" of FIG. 10, a touch fastener being easily peeled off means that even a powerless wearer does not have difficulty in using a touch fastener and the fabric itself having the loop face of a touch fastener is hard, whereby it is difficult to lose a shape.

Further, a touch fastener being not easily peeled off means that at the time of the wearer's movement, there is no case where the hook face of a touch fastener is separated from the loop face due to the movement of a joint or the expansion of a muscle in a site on which the bandage is worn, whereas the pile yarns are pulled out from the fabric having the loop face of a touch fastener due to a strong engaging force between the hook face and the loop face of a touch fastener, and thus, in a case where a touch fastener is peeled off, the pile yarns project from the fabric, thereby causing fluffing of the fabric.

Further, with respect to the evaluation item "close contact property of fabric" of FIG. 10, in a case where the maximum elongation of the fabric is small, the fabric cannot follow the movement of a muscle or the skin, and therefore, a cloth does not come into close contact with the skin and skin resistance is reduced, and thus it is considered that the effect of the bandage is weakened, and in a case where the maximum elongation of the fabric is large, a cloth is easily fixed in close contact with the skin and fits to the movement of the skin or a muscle, and thus it is considered that the effect of the bandage is easily obtained.

Further, with respect to the evaluation item "ease of winding" of FIG. 10, in a case where the maximum elongation of the fabric is small, it is difficult for the fabric to conform to the curved surface of the skin, and thus it is difficult to wind the main body part 10. Further, in a case where the maximum elongation of the fabric is large, the fabric is easily fixed in close contact with the skin and easily fits to the movement of the skin or a muscle. However, for effective wearing, it is necessary to wind the main body part 10 while fully extending it. However, if the main body part 10 is fully extended, the distance between the hand holding the other end 10b of the main body part 10 and the first anchor part 20 becomes longer, and therefore, the wearing and winding on the knee joint becomes difficult. Further, it becomes difficult to fix the other end 10b of the main body part 10 to a predetermined position of the first anchor part 20, and therefore, a movement to wind the main body part 10 while performing seeking so as to be able to fix the other end 10b of the main body part 10 to a predetermined position is performed.

Further, with respect to the evaluation item "ease of adjustment of fixing force" of FIG. 10, in a case where the maximum elongation of the fabric is small, it is suitable for strong fixing. However, an adjustable range of the fixing force is narrow, and therefore, adjustment of the fixing force becomes difficult for a powerless wearer.

Further, with respect to the evaluation item "difficulty of fabric folding" of FIG. 10, in a case where the maximum elongation of the fabric is small, a texture is close, and therefore, there is also stiffness of the fabric, and thus it is difficult for the fabric to be folded. Further, in a case where the maximum elongation of the fabric is large, a texture is rough, and therefore, the fabric has an easily foldable weave, and thus it is considered that due to the fabric being folded, the structure of the main body part 10 is weakened.

In the evaluation items as described above, in Example 2, good evaluation results were obtained in almost all the evaluation items, as shown in FIG. 10.

Further, in Example 3, although the fixing force was weak, good evaluation results were obtained in other evaluation items.

Further, in Example 1, although there was a pain and the close contact property of the fabric was poor, good evaluation results were obtained in other evaluation items. In contrast, in Comparative Example 1 and Comparative Example 2, poor evaluation results were obtained in most of the evaluation items.

From the above, as the overall evaluation results, it is found that Example 1 (maximum elongation: 45%), Example 2 (maximum elongation: 60%), and Example 3 (maximum elongation: 75%), in which the average score is two or more points, are optimal as the main body part 10.

That is, with respect to the maximum elongation in the warp direction in the main body part 10 of the knee joint bandage 100 according to this embodiment, a range of 40% to 80% is preferable, a range of 45% to 75% is more preferable, and the most preferred is 60%.

Next, the first anchor part 20 of the knee joint bandage 100 according to this embodiment will be described based on the test results of a durability test (peeling strength) of a touch fastener.

In addition, in the durability test (peeling strength) of a touch fastener of the first anchor part 20, an evaluation was performed by using the first anchor part 20 woven under the condition that the thickness of the elastic yarn 1c was changed from 840 deniers to 560 deniers and the number of times of picking (the number) of the weft 2 (the weft ground yarn 2a and the fusion yarn 2b) was in a range of 30.8 times (each 30.8 pieces) per 2.54 cm (1 inch) to 36.9 times (each 36.9 pieces) per 2.54 cm (1 inch), similar to the quality of the materials of the warp 1 and the weft 2 and the number of times of picking (the number) of the weft 2 of the main body part 10, so as to correspond to Example 2 (the main body part 10 in which the maximum elongation in the warp direction is 60%) in which the most favorable results were obtained from the evaluation results of the above-described sensory evaluation. Further, as comparative examples, commercially available stretchable fabrics (hereinafter, respectively referred to as Comparative Example 3, Comparative Example 4, and Comparative Example 5) made with the quality of the materials of the warp 1 and the weft 2 and the number of times of picking (the number) of the weft 2 shown in Table 2 below were used. In addition, Comparative Example 3 does not have a loop face as a touch fastener, and therefore, Comparative Example 3 is not provided with a pile yarn in a warp and a fusion yarn in a weft.

TABLE 2

| | Quality of material | | | | | Number of times of picking | | | |
|---|---|---|---|---|---|---|---|---|---|
| | Warp | | | Weft | | (Number) | | | |
| | Warp ground yarn | Pile yarn | Elastic yarn | Weft ground yarn | Fusion yarn | of weft [times/ inch] | Thickness [mm] | Hardness | Maximum elongation [%] |
| Example 2 | WN100/2 | 210D-10F | 560D | EW150D | Elder 100D | 36.9 | 2.1 | Slightly soft | 60 |
| Comparative Example 3 | WN100/2 | — | 1120D | Nylon mono- filament No. 1 | — | 37.0 | 1.7 | Soft | 130 |
| Comparative Example 4 | WN100/2 | 210D-7F | 1120D | EW300D | Elder 100D | 43.6 | 2.2 | Normal | 90 |
| Comparative Example 5 | WN100/2 | 210D-15F | 1120D | EW300D | Elder 100D | 25.8 | 3.3 | Hard | 100 |

Further, the major difference between Example 2 and Comparative Examples 3 to 5 is a difference in the filament count of the pile yarn, in which Example 2 has 10 pieces of filaments, whereas Comparative Example 4 has 7 pieces of filaments, Comparative Example 5 has 15 pieces of filaments, and Comparative Example 3 does not use a pile yarn (does not have a loop face of a touch fastener).

The durability test (peeling strength) of a touch fastener is based on Japanese Industrial Standards JIS L3416, "touch fastener", 7.4.2 "peeling strength", and the experimental results obtained by carrying out a repeat of adhesion and peeling 1000 times are shown in Table 3 below.

therefore, Example 2 is advantageous in terms of a long-term continuing use as the knee joint bandage 100.

Further, the filament count of the pile yarn being high means that the hooks of a touch fastener are easily engaged with the loops and the retention rate is increased, while the maximum elongation is lowered.

In Comparative Example 5, the filament count of the pile yarn is higher than the filament count of the pile yarn of Example 2. However, resin processing is applied in order to prevent fluffing of external appearance, and therefore, it becomes difficult for the hooks of a touch fastener to be engaged with the loops, and the initial peeling strength and

TABLE 3

| | Effective width of fastener [cm] | Peeling strength [N/cm] | | Retention rate [%] (peeling strength after durability test/initial peeling strength × 100) | Change in appearance after durability test |
|---|---|---|---|---|---|
| Example 2 | 4.7 | Initial After durability test | 0.358 0.649 | 181 | Loop elongation which is less (than Comparative Example 5) is recognized. |
| Comparative Example 3 | 4.8 | Initial After durability test | 0.996 0.825 | 83 | Violent fluffing is recognized. |
| Comparative Example 4 | 4.7 | Initial After durability test | 0.281 0.254 | 90 | Noticeable change is not recognized. |
| Comparative Example 5 | 2.8 | Initial After durability test | 0.326 0.537 | 165 | Slight loop elongation is recognized. |

In Example 2, as shown in Table 3, the retention rate (the percentage of peeling strength after durability test with respect to initial peeling strength) is the highest, compared to Comparative Examples 3 to 5, and thus it is found that Example 2 is optimal as the first anchor part 20 which is used in the knee joint bandage 100 which is wound around the knee and then engaged with the hooks of a touch fastener.

In particular, in Example 2, the peeling strength after durability test becomes larger with respect to the initial peeling strength (the retention rate exceeds 100%), and the retention rate become lower than the initial peeling strength and the retention rate of Example 2.

As described above, in the knee joint bandage 100, the main body part 10 (the first supporting part 12 and the second supporting part 13) supports the patella of a wearer toward the thigh side from the lower leg side and supports the medial collateral ligament, whereby it is possible to facilitate the movement of the quadriceps muscle and suppress the deflection to right and left of the knee. That is, the main body part 10 (the first supporting part 12 and the second supporting part 13) supports the patella of a wearer from the lower leg side in an approximately X-shape crossing below the knee of the wearer, thereby being integrated with the movement of the quadriceps muscle, and thus it is possible to play a role like a splint suppressing the deflection to right and left of the knee.

Further, in the knee joint bandage 100, the main body part 10 (the first supporting part 12 and the second supporting part 13) applies a strong pressing force toward the outer surface from the inner surface with respect to the knee of a wearer who wears the knee joint bandage 100, whereby in a case where the knee receives an external force from the outer surface side of the knee joint bandage 100, it is possible to generate a repulsive force toward the outer surface from the inner surface, which alleviates the external force, and thus the knee does not enter the inside due to the external force and it is possible to prevent damage to the medial collateral ligament.

Further, in the knee joint bandage 100, the main body part 10 (the first supporting part 12 and the second supporting part 13) supports the outer surfaces of the thigh and the knee of a wearer who wears the knee joint bandage 100, thereby providing a balance with the pressing force which is applied to the inner surface by the main body part 10 (the first supporting part 12 and the second supporting part 13), and thus it is possible to maintain a stable standing state of the wearer.

Further, the mounting of a knee supporter provided with band-shaped supporting parts equivalent to the first supporting part 12 and the second supporting part 13 of the knee joint bandage 100 is effective as a method for supporting the knee joint of a wearer. That is, due to mounting the knee supporter (for example, the knee joint bandage 100) so as to raise the patella of a wearer from the lower side to the upper side by disposing the band-shaped supporting parts (the first supporting part 12 and the second supporting part 13) on both right and left sides from the lower side of the part corresponding to the patella of the wearer, the band-shaped supporting parts support the patella of the wearer so as to raise it from the lower side to the upper side while gripping the patella of the wearer from the right and left, and therefore, it is possible to exhibit the operation and effects of reducing a burden on the knee region of the wearer by smoothly assisting in the movement of the quadriceps muscle.

Further, the mounting of a knee supporter in which a band-shaped anchor part having a loop face, which is equivalent to the first anchor part 20 of the knee joint bandage 100, is provided at the knee supporter provided with the band-shaped supporting parts is more effective as a method for supporting the knee joint of a wearer. That is, due to mounting the knee supporter so as to raise the patella from the lower side to the upper side by making one end of the band-shaped supporting part (for example, the second supporting part 13) be engaged with the loop face of the band-shaped anchor part (for example, the first anchor part 20) fixed to the thigh of a wearer, the knee supporter is reliably fixed to the position of the knee joint of the wearer, and therefore, it is possible to more effectively exhibit the operation and effects of the band-shaped supporting part.

Further, in the knee joint bandage 100 shown in FIG. 2, for example, a green yarn is used for the warp ground yarn 1a of the warp 1 of the main body part 10, a black yarn is used for the warp ground yarn 1a of the warp 1 of the first anchor part 20, black yarns are used for the pile yarns 1b of the warps 1 of the main body part 10 and the first anchor part 20, black yarns are used for the elastic yarns 1c of the warps 1 of the main body part 10 and the first anchor part 20, black yarns are used for the wefts 2 of the main body part 10 and the first anchor part 20, and as shown in FIG. 7, with respect to the shared weft 2, the warp ground yarn 1a is made to float and the pile yarn 1b is made to sink, whereby a green pattern 14 is formed on a black front ground face of the main body part 10, and a portion of the back ground face of the main body part 10, which corresponds to the pattern 14 of the front ground face of the main body part 10, appears as black on a green back ground face of the main body part 10.

Further, in the knee joint bandage 100, there is no limitation to these colors, and for example, it is conceivable that a yarn having any one color of seven colors (red, orange, yellow, green, blue, indigo, and violet) which are the rainbow colors is used for the pile yarn 1b of the warp 1 of the main body part 10 and the front ground face except for the pattern 14 of the main body part 10 is made to have any one color of the rainbow colors. In this way, the knee joint bandages 100 can encourage a consumer's willingness to buy with product groups with color variation of seven colors.

Further, in the knee joint bandage 100, for example, the front ground face except for the pattern 14 of the main body part 10 is made to have a fluorescent color by using a fluorescent colored yarn for the pile yarn 1b of the warp 1 of the main body part 10, whereby a consumer's willingness to buy is encouraged, and the knee joint bandage 100 is worn during going out at night, whereby it is visible by being illuminated by the headlights of an automobile or the like, and thus it can be expected to contribute to the safety and disaster prevention as well.

Second Embodiment of the Present Invention

Figure 11:
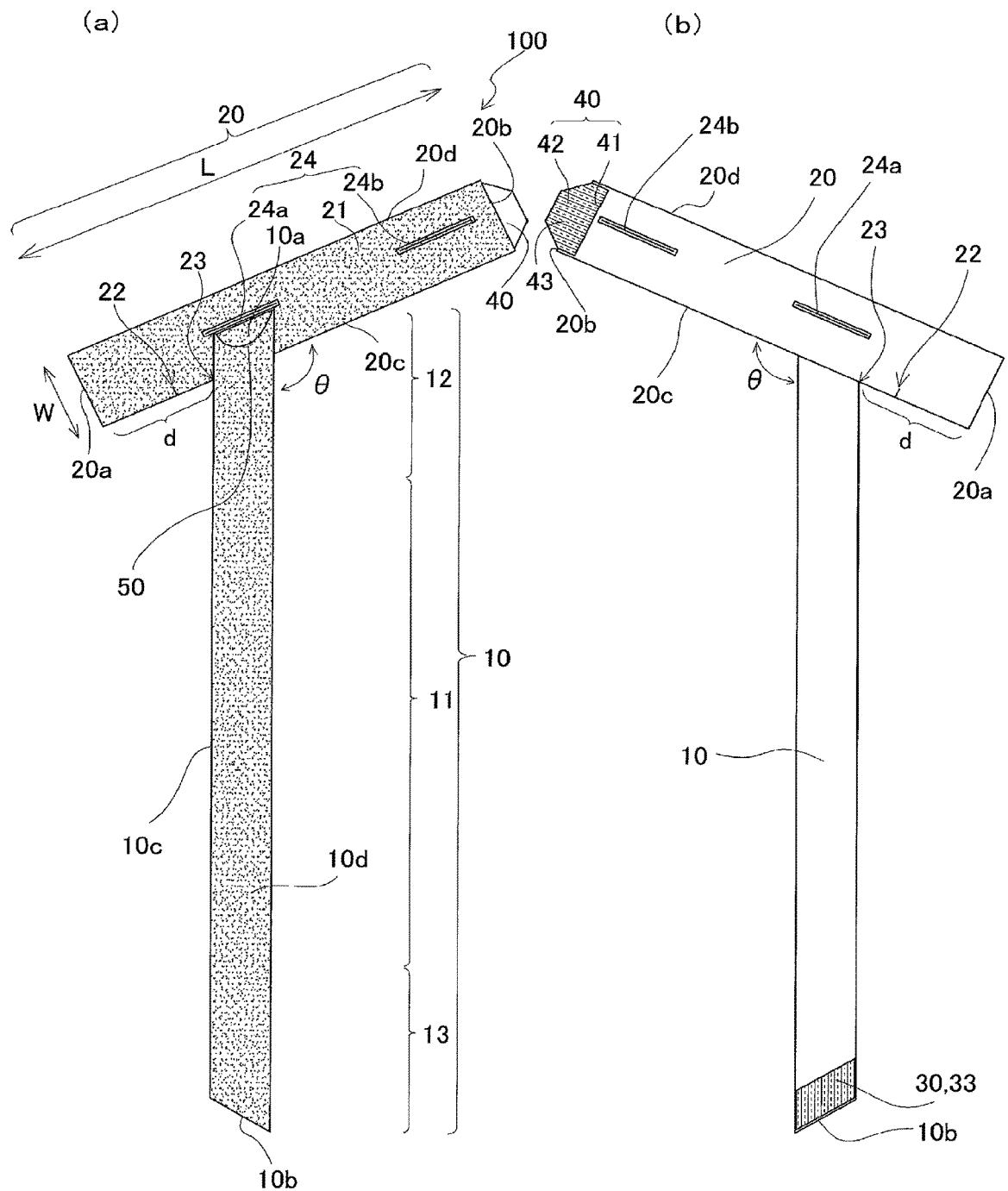
FIG. 11(a) is a front view showing a schematic configuration of a knee joint bandage according to a second embodiment.
FIG. 11(b) is a back view of the knee joint bandage shown in FIG. 11(a).
Figure 12:
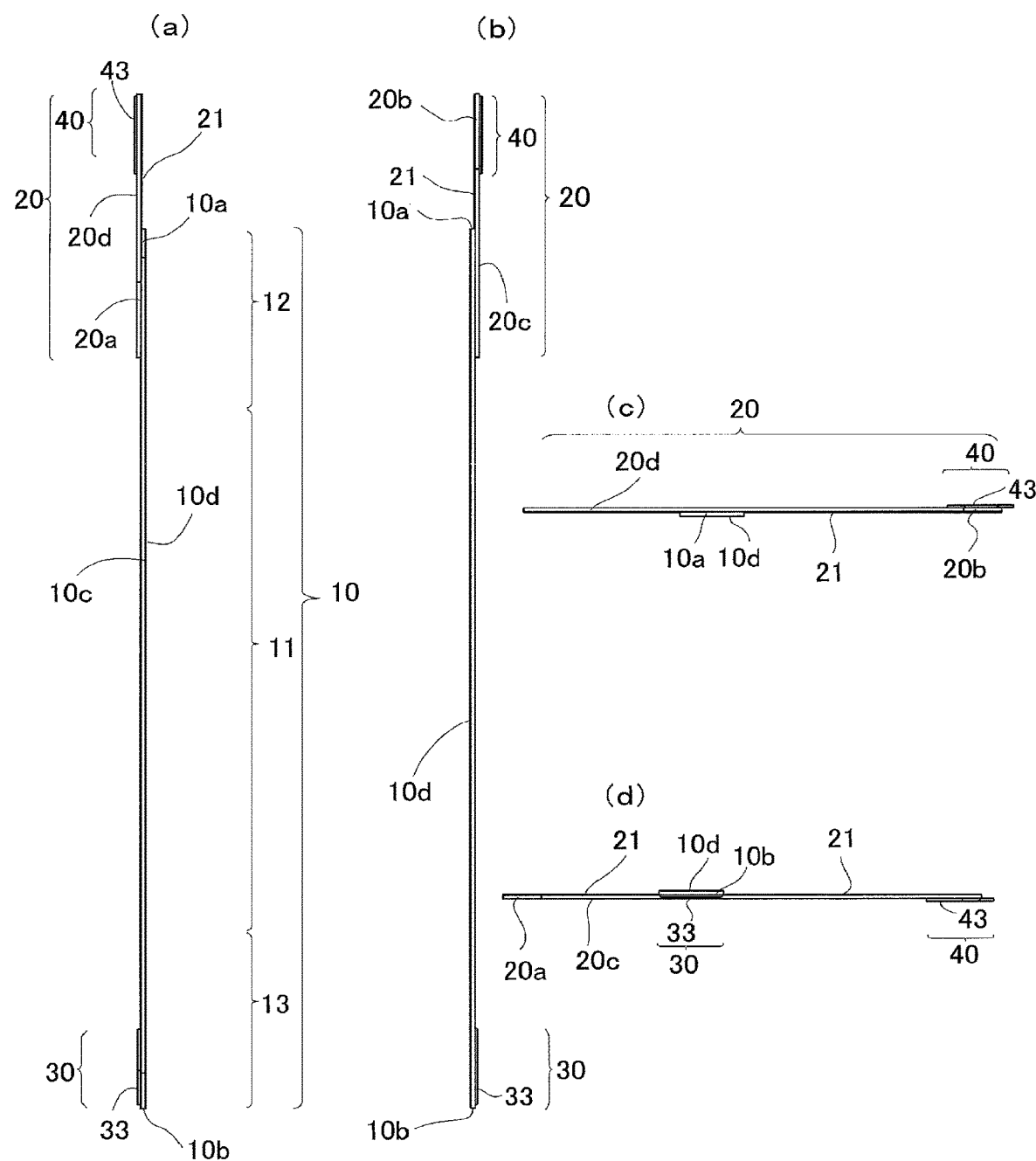
FIG. 12(a) is a left side view of the knee joint bandage shown in FIG. 11(a)
FIG. 12(b) is a right side view of the knee joint bandage shown in FIG. 11(a)
FIG. 12(c) is a plan view of the knee joint bandage shown in FIG. 11(a)
FIG. 12(d) is a bottom view of the knee joint bandage shown in FIG. 11(a).

FIG. 11(a) is a front view showing a schematic configuration of a knee joint bandage according to a second embodiment, and FIG. 11(b) is a back view of the knee joint bandage shown in FIG. 11(a). FIG. 12(a) is a left side view of the knee joint bandage shown in FIG. 11(a), FIG. 12(b) is aright side view of the knee joint bandage shown in FIG. 11(a), FIG. 12(c) is a plan view of the knee joint bandage shown in FIG. 11(a), and FIG. 12(d) is a bottom view of the knee joint bandage shown in FIG. 11(a). FIG. 13(a) is an explanatory diagram of the wearing state of the knee joint bandage shown in FIGS. 11 and 12 when viewed from the right side, FIG. 13(b) is an explanatory diagram of the wearing state of the knee joint bandage shown in FIGS. 11 and 12 when viewed from the front side, FIG. 13(c) is an explanatory diagram of the wearing state of the knee joint bandage shown in FIGS. 11 and 12 when viewed from the back side, and FIG. 13(d) is an explanatory diagram of the wearing state of the knee joint bandage shown in FIGS. 11 and 12 when viewed from the left side. In FIGS. 11, 12, and 13, the same reference numerals as those in FIG. 1 or 3 denote identical or corresponding parts, and description thereof is omitted.

The first anchor part 20 is provided with a slit 24 extending in the longitudinal direction L (the warp direction) of the main body part 10, at least between an upper side 20d of the first anchor part 20 and one end 10a of the main body part 10 in a state where the first anchor part 20 has been fastened around the thigh of a wearer (refer to FIG. 13(a)), and/or between the upper side 20d of the first anchor part 20 and the other end 10b of the main body part 10 in a state where the first engaging part 30 has been engaged with the first anchor part 20 (refer to FIG. 13(d)), as shown in FIGS. 11 and 13.

In addition, in the following description, as necessary, the slit 24 which exists between the upper side 20d of the first anchor part 20 and one end 10a of the main body part 10 in a state where the first anchor part 20 has been fastened around the thigh of a wearer is referred to as a "one end-side slit 24a", and the slit 24 which exists between the upper side 20d of the first anchor part 20 and the other end 10b of the main body part 10 in a state where the first engaging part 30 has been engaged with the first anchor part 20 is referred to as "the other end-side slit 24b".

Further, the slit 24 according to this embodiment has a length in a range of 5 cm to 9 cm, the distance from the lower side 20c of the first anchor part 20 to the slit 24 is in a range of 3 cm to 5 cm, and the distance from the upper side 20d of the first anchor part 20 to the slit 24 is in a range of 2 cm to 4 cm. However, if the slit 24 is longer than the length of one end 10a (the other end 10b) of the main body part 10 and the first anchor part 20 functions as an anchor of the main body part 10, there is no limitation to the position, the size (the length or the width), and the number of the slit 24 shown in FIG. 11.

In the main body part 10, as shown in FIG. 11(a), one end 10a is cut so as to be substantially parallel to the lower side 20c of the first anchor part 20 (refer to FIG. 13(a)), similar to that in the first embodiment, and the other end 10b is cut so as to form the main body part 10 having an isosceles trapezoidal shape, and in a case where a wearer has correctly worn the knee joint bandage 100, the other end 10b becomes substantially parallel to the lower side 20c of the first anchor part 20 (refer to FIG. 13(d)).

The first engaging part 30 has a planar shape which is a parallelogram and is sewn to the back ground face of the main body part 10 without protruding from the other end 10b of the main body part 10, as shown in FIG. 11(b).

For this reason, as shown in FIG. 13(d), in a case where a wearer has correctly worn the knee joint bandage 100, the other end 10b of the main body part 10 is located below the other end-side slit 24b and becomes substantially parallel to the lower side 20c of the first anchor part 20, and thus the first engaging part 30 does not lay across the other end-side slit 24b.

Further, the second embodiment is different from the first embodiment only in that the slit 24 is newly provided in the first anchor part 20 of the knee joint bandage 100 and the shapes of the other end 10b of the main body part 10 and the first engaging part 30 are changed, and exhibits the operation and effects which are the same as those of the first embodiment except for the operation and effects by the slit 24, which will be described later.

In the knee joint bandage 100 according to this embodiment, the first anchor part 20 is provided with the slit 24, whereby with respect to the tensile stress from the main body part 10, a force is dispersed in the fabric on the lower side 20c side of the first anchor part 20 with the slit 24 as a boundary and the influence on the fabric on the upper side 20d side of the first anchor part 20 is suppressed, and thus it is possible to maintain an anchor function by the fabric on the upper side 20d side of the first anchor part 20.

Further, in the knee joint bandage 100 according to this embodiment, the first anchor part 20 is provided with the slit 24, whereby with respect to the flexion of the knee joint of a wearer, the fabric on the lower side 20c side of the first anchor part 20 moves down to follow the flexion while supporting is performed by the fabric on the upper side 20d side of the first anchor part 20, and with respect to the extension of the knee joint of a wearer, the fabric on the lower side 20c side of the first anchor part 20 moves up with a restoring force, and thus the operation and effects in which the first anchor part 20 can flexibly respond to the movement of the knee joint of a wearer are exhibited.

Further, the knee joint bandage 100 according to this embodiment is provided with either of the one end-side slit 24a or the other end-side slit 24b, whereby the operation and effects described above are newly exhibited with respect to the knee joint bandage 100 according to the first embodiment which is not provided with the slit 24.

However, in a case where the slit 24 is provided on only one side, sliding-down of the first anchor part 20 on the fabric side where the slit 24 is provided, due to the tensile stress from the main body part 10, is suppressed, whereas sliding-down of the first anchor part 20 on the fabric side where the slit 24 is not provided occurs, whereby a balance of the crossing portion by the first supporting part 12 and the second supporting part 13 below the knee is not maintained and the operation and effects by the slit 24 are halved. For this reason, in the knee joint bandage 100 according to this embodiment, it is preferable that two slits 24; the one end-side slit 24a and the other end-side slit 24b, are provided.

Third Embodiment of the Present Invention

Figure 14:
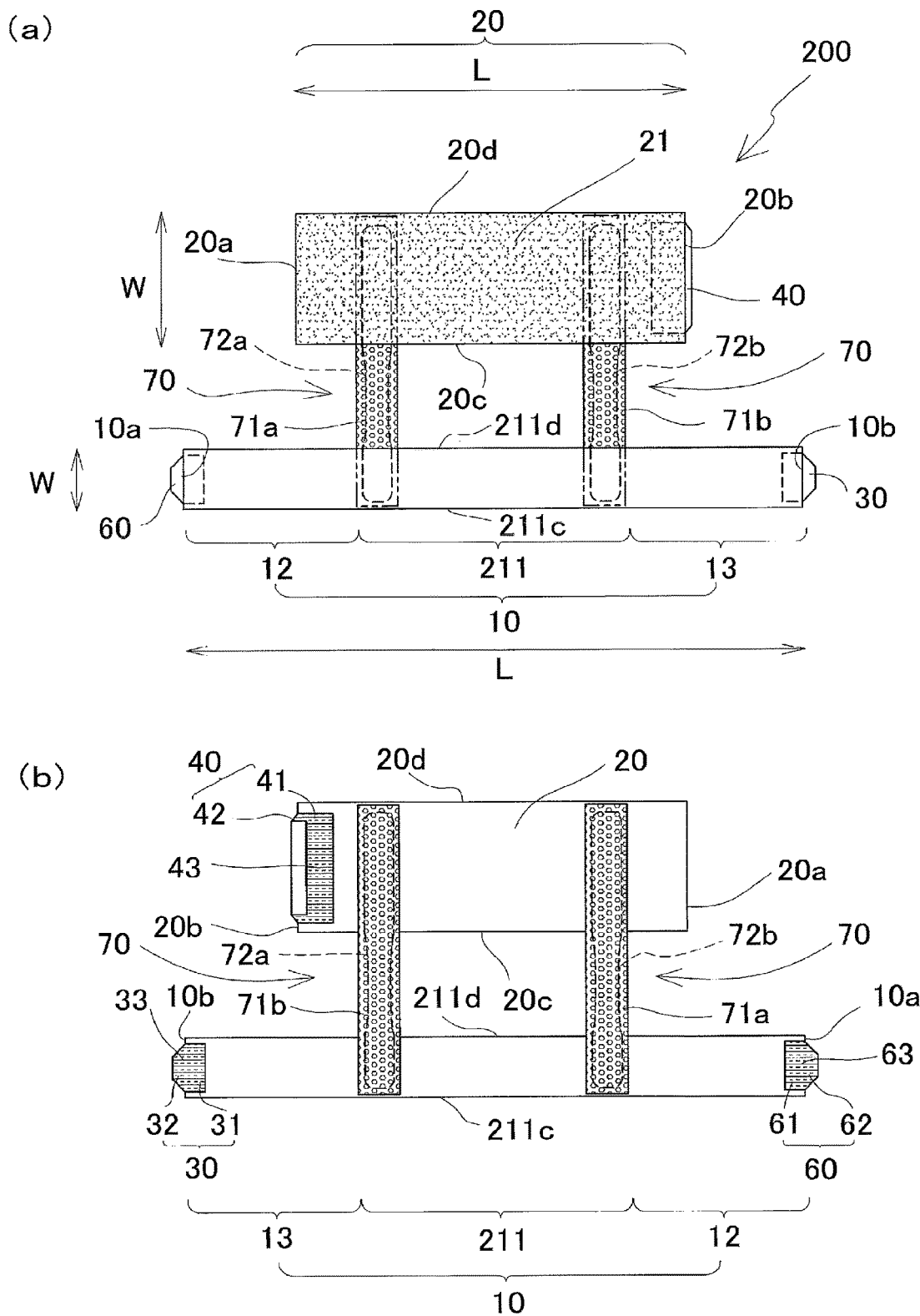
FIG. 14(a) is a front view showing a schematic configuration of a knee joint supporter according to a third embodiment.
FIG. 14(b) is a back view of the knee joint supporter shown in FIG. 14(a).
Figure 15:
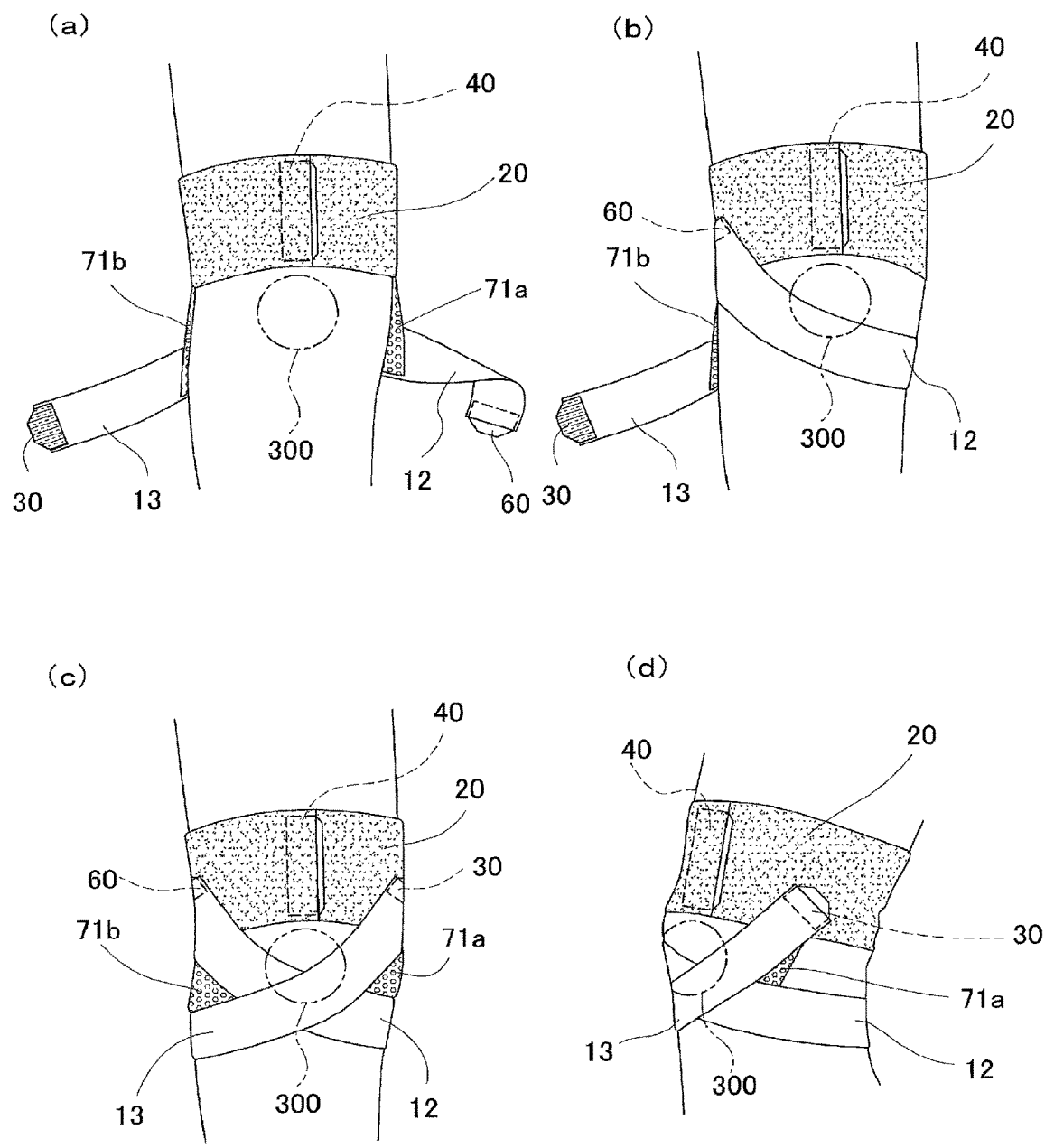
FIG. 15(a) is an explanatory diagram showing a state where a first anchor part of the knee joint supporter shown in FIG. 14 is fastened around the thigh.
FIG. 15(b) is an explanatory diagram showing a state where a third engaging part of a first supporting part of the knee joint supporter shown in FIG. 14 is engaged with the first anchor part.
FIG. 15(c) is an explanatory diagram showing a state where the first engaging part of a second supporting part of the knee joint supporter shown in FIG. 14 is engaged with the first anchor part.
FIG. 15(d) is an explanatory diagram of the wearing state of the knee joint supporter shown in FIG. 14 when viewed from the right side.
Figure 16:
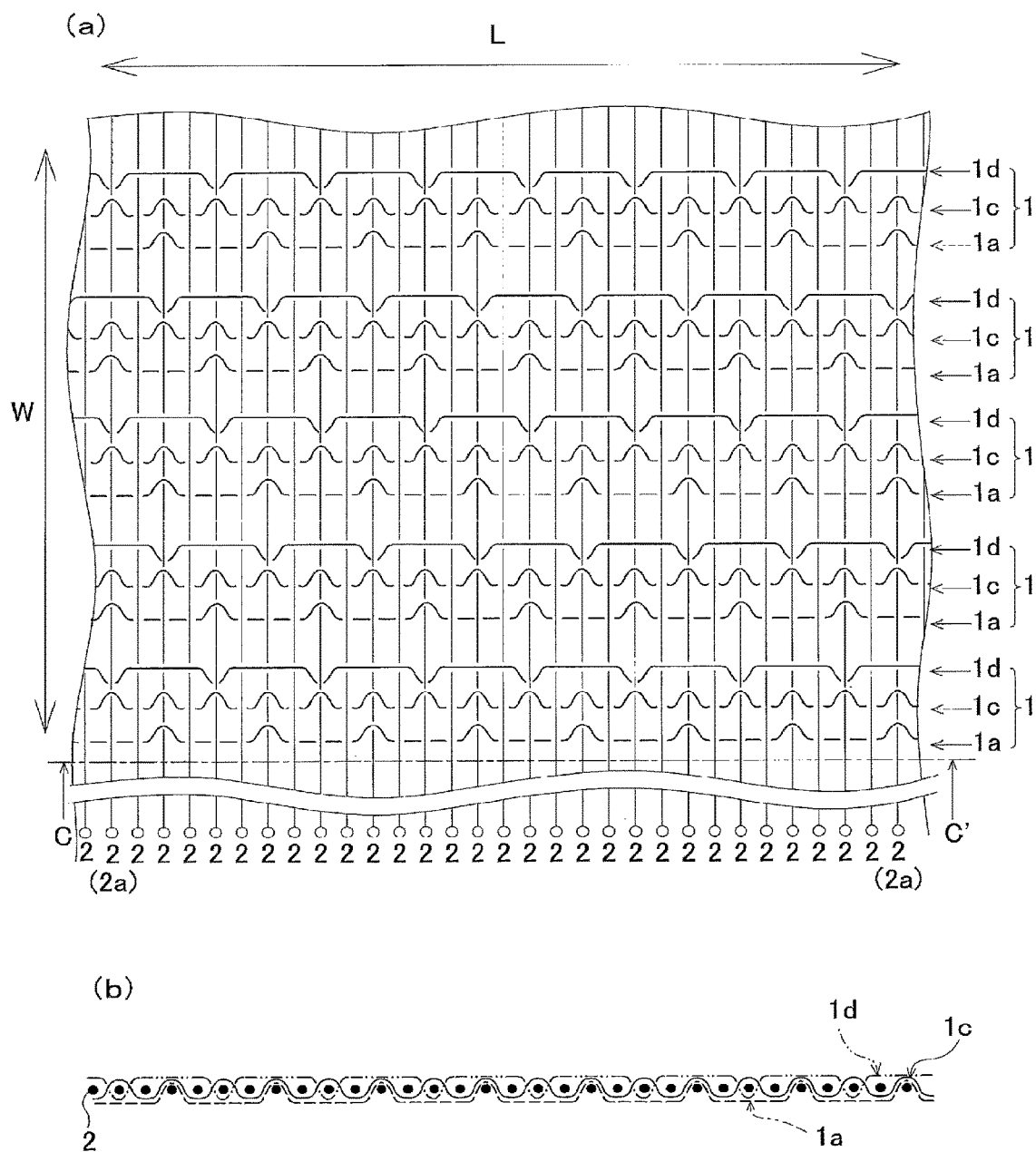
FIG. 16(a) is an explanatory diagram for describing an example of a fabric weave of a front ground face of the main body part shown in FIG. 14.
FIG. 16(b) is a cross-sectional view taken along line C-C' and viewed in the direction of an arrow, of the fabric weave shown in FIG. 16(a).
Figure 17:
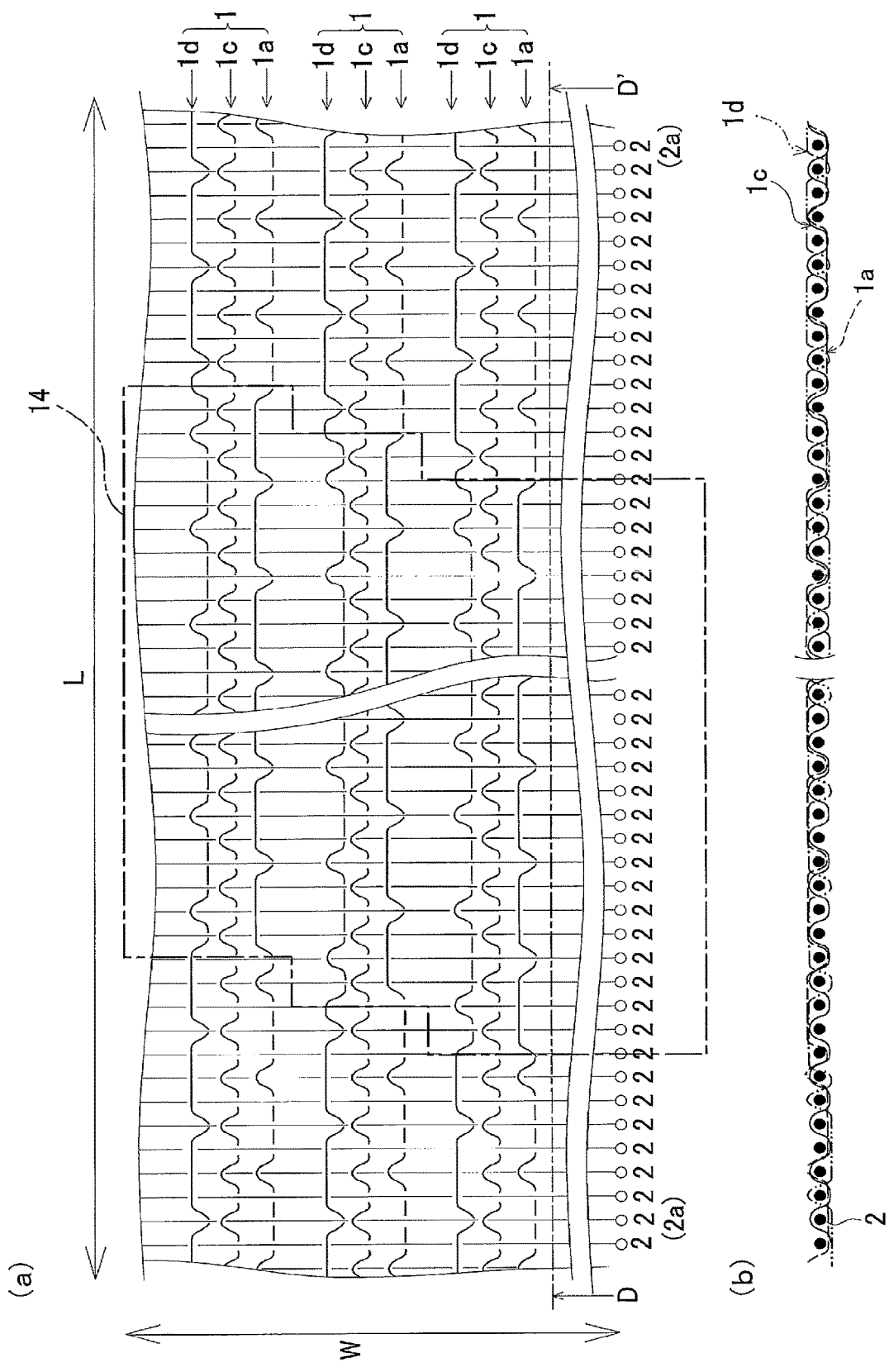
FIG. 17(a) is an explanatory diagram for describing an example of a fabric weave of a pattern part of a main body part which does not have a loop face of a touch fastener.
FIG. 17(b) is a cross-sectional view taken along line D-D' and viewed in the direction of an arrow, of the fabric weave shown in FIG. 17(a).
Figure 19:
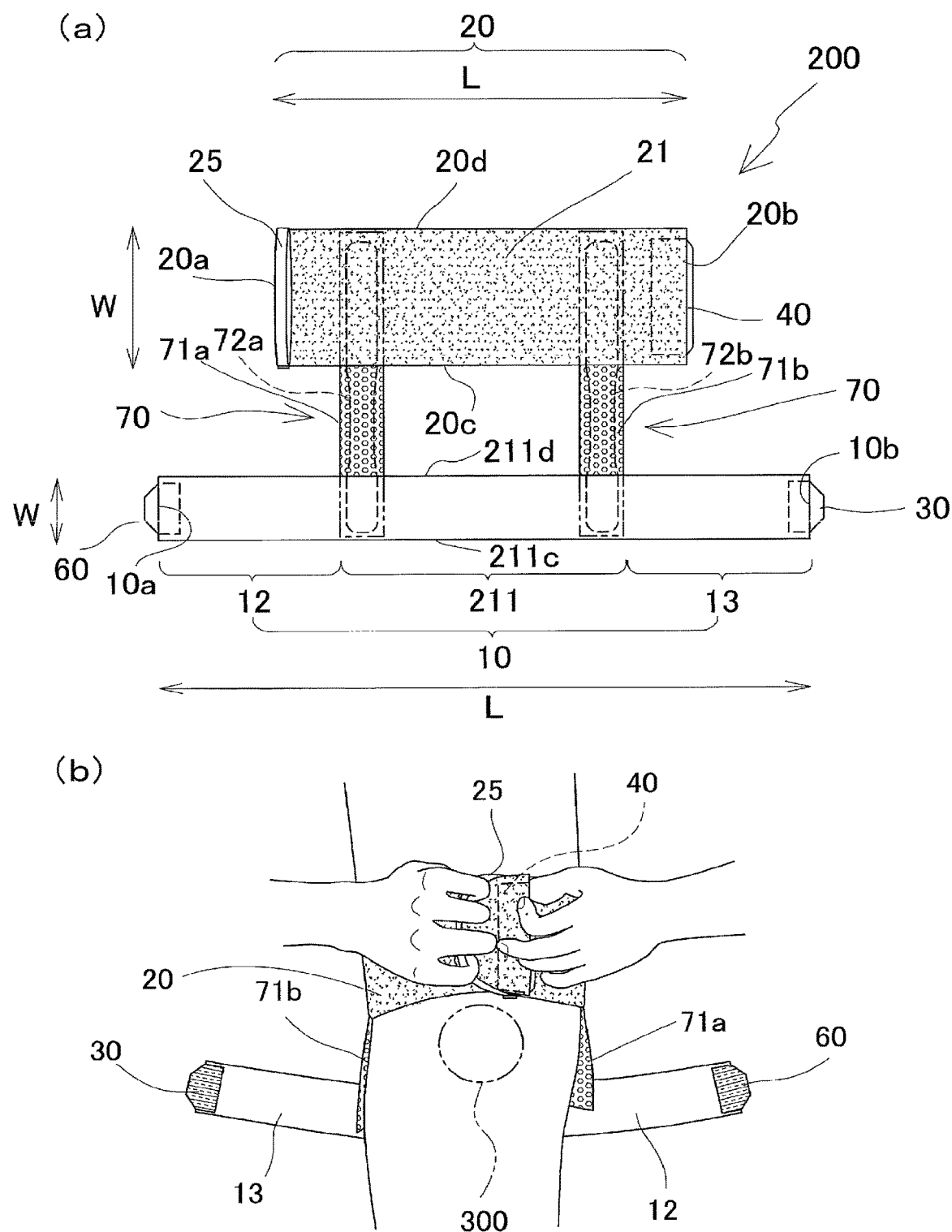
FIG. 19(a) is a front view showing a schematic configuration of still another knee joint supporter according to the third embodiment.
FIG. 19(b) is an explanatory diagram showing a method of fastening a first anchor part of the knee joint supporter shown in FIG. 19(a) around the thigh.

FIG. 14(a) is a front view showing a schematic configuration of a knee joint supporter according to a third embodiment, and FIG. 14(b) is a back view of the knee joint supporter shown in FIG. 14(a). FIG. 15(a) is an explanatory diagram showing a state where a first anchor part of the knee joint supporter shown in FIG. 14 is fastened around the thigh, FIG. 15(b) is an explanatory diagram showing a state where a third engaging part of a first supporting part of the knee joint supporter shown in FIG. 14 is engaged with the first anchor part, FIG. 15(c) is an explanatory diagram showing a state where a first engaging part of a second supporting part of the knee joint supporter shown in FIG. 14 is engaged with the first anchor part, and FIG. 15(d) is an explanatory diagram of the wearing state of the knee joint supporter shown in FIG. 14 when viewed from the right side. FIG. 16(a) is an explanatory diagram for describing an example of a fabric weave of a front ground face of the main body part shown in FIG. 14, and FIG. 16(b) is across-sectional view taken along line C-C' and viewed in the direction of an arrow, of the fabric weave shown in FIG. 16(a). FIG. 17(a) is an explanatory diagram for describing an example of a fabric weave of a pattern part of a main body part which does not have a loop face of a touch fastener, and FIG. 17(b) is a cross-sectional view taken along line D-D' and viewed in the direction of an arrow, of the fabric weave shown in FIG. 17(a). FIG. 18(a) is a front view showing a schematic configuration of another knee joint supporter according to the third embodiment, and FIG. 18(b) is an explanatory diagram showing a state where a first anchor part of the knee joint supporter shown in FIG. 18(a) is fastened around the thigh and a second anchor part is fastened around the lower leg. FIG. 19(a) is a front view showing a schematic configuration of still another knee joint supporter according to the third embodiment, and FIG. 19(b) is an explanatory diagram showing a method of fastening a first anchor part of the knee joint supporter shown in FIG. 19(a) around the thigh. In FIGS. 14 to 19, the same reference numerals as those in FIGS. 1 to 3 denote identical or corresponding parts, and description thereof is omitted.

A knee joint supporter 200 according to the present invention comprises: the first anchor part 20 which is woven in a fabric having the loop face 21 of a touch fastener and is fastened around the thigh of a wearer; the main body part 10 which is a band-shaped fabric and is composed of a second anchor part 211 which is disposed at least below the popliteal region of the wearer, the first supporting part 12 which is disposed in a taut state on one side from below a part corresponding to the patella 300 of the wearer, and the second supporting part 13 which is disposed in a taut state on the other side of the part corresponding to the patella 300 of the wearer to cross the first supporting part 12 below the part corresponding to the patella 300 of the wearer; and connection parts 70 which are joined to the first anchor part 20 and the second anchor part 211, thereby integrating the first anchor part 20 and the main body part 10, as shown in FIGS. 14 and 15.

In addition, the second anchor part 211 according to this embodiment corresponds to the winding part 11 according to the first embodiment and the second embodiment, and also in this embodiment, the second anchor part 211 is provided between the first supporting part 12 and the second supporting part 13, thereby configuring the main body part 10, and the first supporting part 12, the second anchor part 211, and the second supporting part 13 have straight line shapes having the same width.

Further, the connection parts 70 according to this embodiment are a pair of left and right bag-shaped parts 71 each containing a support 72 and are disposed in a taut state on both sides of the part corresponding to the patella of a wearer.

In addition, in the following description, in order to distinguish the left and right bag-shaped parts 71 (supports 72), in FIG. 14(*a*), the bag-shaped part 71 (the support 72) of the left side is referred to as a left bag-shaped part 71*a* (a left support 72*a*) and the bag-shaped part 71 (the support 72) of the right side is referred to as a right bag-shaped part 71*b* (a right support 72*b*).

Further, the knee joint supporter 200 according to the present invention is provided with: the first engaging part 30 which is joined to an end portion of the second supporting part 13, which is the other end 10*b* of the main body part 10, and has a hook face 33 of a touch fastener, which is detachably stuck to the loop face 21 of the first anchor part 20; the second engaging part 40 which is joined to one end 20*a* or the other end 20*b* of the first anchor part 20 and has a hook face 43 of a touch fastener, which is detachably stuck to the loop face 21 of the first anchor part 20; and a third engaging part 60 which is joined to an end portion of the first supporting part 12, which is one end 10*a* of the main body part 10, and has a hook face 63 of a touch fastener, which is detachably stuck to the loop face 21 of the first anchor part 20.

Further, the third engaging part 60 (the hook face 63) according to this embodiment is provided on the back ground face side of one end 10*a* of the main body part 10 in terms of the ease of attachment and detachment and the degree of freedom of an engaging position.

Further, the third engaging part 60 according to this embodiment has a planar shape of a combination of, for example, a rectangle and an isosceles trapezoid, as shown in FIG. 14(*b*), in which a rectangular portion 61 is sewn to one face (the back ground face) of the main body part 10 and an isosceles trapezoid portion 62 protrudes from one end 10*a* of the main body part 10.

In this manner, in the third engaging part 60, the isosceles trapezoid portion 62 protrudes from one end 10*a* of the main body part 10, thereby becoming thinner by an amount that does not overlap the main body part 10, whereby it is easy to grip the isosceles trapezoid portion 62 with the fingers of a wearer, and thus it is possible to easily attach and detach the hook face 63 with respect to the loop face 21 of the first anchor part 20.

Further, the knee joint supporter 200 has a double use for both the right knee and left knee in which it can be worn on the knee of either of the right foot or the left foot of the wearer.

Further, with respect to the main body part 10 according to the first embodiment and the second embodiment, a case where the main body part 10 has the loop face 10*d* of a touch fastener has been described. However, the main body part 10 according to this embodiment may be a stretchable fabric which does not have the loop face 10*d* of a touch fastener, as shown in FIG. 14.

Further, the maximum elongation in the warp direction (the longitudinal direction L) of the main body part 10 according to this embodiment does not affect the sensory evaluation described in the first embodiment even if the main body part 10 is a stretchable fabric which does not have the loop face 10*d* of a touch fastener, and similar to the first embodiment and the second embodiment, it is preferable that the maximum elongation is set to be in a range of 40% to 80%, a range of 45% to 75% is more preferable, and the most preferred to 60%.

In this case, the main body part 10 does not need the pile yarn 1*b* forming the loop face 10*d* and does not need the fusion yarn 2*b* holding the loops by the pile yarn 1*b*.

In particular, the main body part 10 according to this embodiment uses, instead of the pile yarn 1*b* configuring the warp 1, a warp ground yarn 1*a* (hereinafter referred to as a second warp ground yarn 1*d*) in which float-sink with respect to the weft 2 is reversed with respect to that in the above-described warp ground yarn 1*a* (hereinafter, the warp ground yarn 1*a* of the main body part 10 is referred to as a "first warp ground yarn 1*a*").

That is, the warp 1 is provided with the first warp ground yarn 1*a* which configures one face (for example, the back ground face) of the fabric along with the weft 2, the elastic yarn 1*c* which provides stretchability in the warp direction, and the second warp ground yarn 1*d* which configures the other face (for example, the front ground face) of the fabric along with the weft 2, as shown in FIG. 16.

Further, the weft 2 is provided with the weft ground yarn 2*a* which configures the back ground face of the fabric along with the first warp ground yarn 1*a*.

Further, in FIGS. 16(*b*) and 17(*b*), on the basis of the wefts 2 which are provided in parallel, the upper side is the front ground face and the lower side is the back ground face.

Further, in the main body part 10, the pattern 14 composed of characters, figures, symbols, or a combination thereof can be partially formed in the front ground face in a jacquard weave which is freely opened, by making the first warp ground yarn 1*a* (for example, a green yarn) of the warp 1 float to the front ground face side (and making the second warp ground yarn 1*d* (for example, a black yarn) sink to the back ground face side) with respect to a plurality of wefts 2 adjacent to each other in the warp direction (the longitudinal direction L) by using a jacquard needle loom.

Next, an example of a fabric weave according to this embodiment will be described by using FIG. 16. That is, the first warp ground yarn 1*a* configures a fabric weave by repeating 1-3 float-sink with respect to the weft 2 (the weft ground yarn 2*a*), in which the first warp ground yarn 1*a* floats so as to pass on the upper side with respect to a single piece of weft 2 (weft ground yarn 2*a*) and sinks so as to pass on the lower side with respect to three pieces of wefts 2 (weft ground yarns 2*a*) adjacent to each other, as shown in FIG. 16(*b*).

Further, the elastic yarn 1*c* configures a fabric weave by repeating 1-1 float-sink with respect to the weft 2 (the weft ground yarn 2*a*), in which the elastic yarn 1*c* floats so as to pass on the upper side with respect to a single piece of weft 2 (weft ground yarn 2*a*) and sinks so as to pass on the lower side with respect to a single piece of weft 2 (weft ground yarn 2*a*), as shown in FIG. 16(*b*).

Further, the second warp ground yarn 1*d* configures a fabric weave by repeating 3-1 float-sink with respect to the weft 2 (the weft ground yarn 2*a*), in which the second warp ground yarn 1*d* floats so as to pass on the upper side with respect to three pieces of wefts 2 (weft ground yarns 2*a*) adjacent to each other and sinks so as to pass on the lower side with respect to a single piece of weft 2 (weft ground yarn 2*a*), as shown in FIG. 16(*b*).

In addition, the fabric weave composed of the first warp ground yarn 1*a*, the elastic yarn 1*c*, and the second warp ground yarn 1*d* shown in FIG. 16 is an example, and there is no limitation to this fabric weave.

Subsequently, an example of a fabric weave of a pattern part according to this embodiment will be described by using FIG. 17. That is, the first warp ground yarn 1*a* forming the pattern 14 configures a fabric weave by repeating 3-1 float-sink with respect to the weft 2 (the weft ground yarn 2*a*), in which the first warp ground yarn 1*a* floats so as to pass on the upper side with respect to three pieces of wefts 2 (weft ground yarns 2*a*) adjacent to each other and sinks so as to pass on the lower side with respect to a single piece of weft 2 (weft ground yarn 2*a*), as shown in FIG. 17(*b*).

Further, the elastic yarn 1*c* forming the pattern 14 configures a fabric weave by repeating 1-1 float-sink with respect to the weft 2 (the weft ground yarn 2*a*), in which the elastic yarn 1*c* floats so as to pass on the upper side with respect to a single piece of weft 2 (weft ground yarn 2*a*) and sinks so as to pass on the lower side with respect to a single piece of weft 2 (weft ground yarn 2*a*), as shown in FIG. 17(*b*).

Further, the second warp ground yarn 1*d* forming the pattern 14 configures a fabric weave by repeating 1-3 float-sink with respect to the weft 2 (the weft ground yarn 2*a*), in which the second warp ground yarn 1*d* floats so as to pass on the upper side with respect to a single piece of weft 2 (weft ground yarn 2*a*) and sinks so as to pass on the lower side with respect to three pieces of wefts 2 (weft ground yarns 2*a*) adjacent to each other, as shown in FIG. 17(*b*).

In addition, the fabric weave composed of the first warp ground yarn 1*a*, the elastic yarn 1*c*, and the second warp ground yarn 1*d* shown in FIG. 17 is an example, and as long as it is possible to form the pattern 14 in the front ground face, there is no limitation to this fabric weave.

Next, an embodiment in which the maximum elongation of the main body part 10 is set to be 60% (1.60 times±0.1) and the maximum elongation of the first anchor part 20 is set to be 95% (1.95 times±0.1) will be described.

With respect to each of the first warp ground yarn 1*a* and the second warp ground yarn 1*d* of the main body part 10 according to this embodiment, a woolly nylon two-fold yarn having a thickness of 100 deniers is preferable, and in the main body part 10 according to this embodiment, it is preferable to use 152 pieces of woolly nylon two-fold yarns for each of the first warp ground yarn 1*a* and the second warp ground yarn 1*d*.

Further, with respect to the warp ground yarn 1*a* of the first anchor part 20 according to this embodiment, a woolly nylon two-fold yarn having a thickness of 100 deniers is preferable, and in the first anchor part 20 according to this embodiment, it is preferable to use 200 pieces of woolly nylon two-fold yarns.

Further, the pile yarn 1*b* of the first anchor part 20 according to this embodiment is a special textured yarn (235T-10F) obtained by twisting 10 pieces of nylon filaments together, then applying heat thereto, and further performing twisting in a direction opposite to the twisting direction of the 10 pieces of nylon filaments, and having a thickness of 235 texes, and in the first anchor part 20 according to this embodiment, it is preferable to use 200 pieces of special textured yarns (235T-10F).

Further, with respect to the elastic yarn 1*c* of the main body part 10 according to this embodiment, a covering yarn obtained by covering a polyurethane yarn (for example, a polyurethane elastic fiber "Lycra (registered trademark) fiber" of Toray Opelontex Co., Ltd.) having a thickness of 560 deniers with two pieces of polyester woolly (EW) single yarns each having a thickness of 150 deniers is preferable, and in the main body part 10 according to this embodiment, it is preferable to use 41 pieces of covering yarns.

Further, with respect to the elastic yarn 1*c* of the first anchor part 20 according to this embodiment, a covering yarn obtained by covering a polyurethane yarn (for example, spandex (polyurethane fiber) "Roica (registered trademark)" of Asahi Kasei Fibers Corporation) having a thickness of 840 deniers with two pieces of polyester woolly (EW) single yarns each having a thickness of 150 deniers is preferable, and in the first anchor part 20 according to this embodiment, it is preferable to use 53 pieces of covering yarns.

Further, with respect to the weft ground yarn 2*a* of the main body part 10 according to this embodiment, it is preferable to use a single piece of polyester woolly yarn (EW) having a thickness of 150 deniers.

Further, the main body part 10 according to this embodiment does not have a loop face of a touch fastener, and therefore, the weft 2 of the main body part 10 is not provided with the fusion yarn 2*b* holding loops by the pile yarn 1*b*. However, the main body part 10 according to this embodiment may have the fusion yarn 2*b* in the weft 2 of the main body part 10 and have a loop face of a touch fastener, similar to the main body part 10 according to the first embodiment.

Further, in the main body part 10 according to this embodiment, a single piece of weft ground yarn 2*a* is picked as the weft 2 by a power loom, and the number of times of picking (the number) of the weft 2 (the weft ground yarn 2*a*) is 33.6 times (33.6 pieces) per 2.54 cm (1 inch).

Further, with respect to the weft ground yarn 2*a* of the first anchor part 20 according to this embodiment, it is preferable to use a single piece of polyester woolly (EW) single yarn having a thickness of 150 deniers.

Further, with respect to the fusion yarn 2*b* of the first anchor part 20 according to this embodiment, it is preferable to use a single piece of nylon thermal fusion yarn (for example, "Elder (registered trademark)" manufactured by Toray Industries, Inc.) having a thickness of 100 deniers.

Further, in the first anchor part 20 according to this embodiment, a single piece of weft ground yarn 2*a* and a single piece of fusion yarn 2*b* are simultaneously picked as the weft 2 by a power loom, and the number of times of picking (the number) of the weft 2 (the weft ground yarn 2*a* and the fusion yarn 2*b*) is 30.8 times (each 30.8 pieces) per 2.54 cm (1 inch).

In this manner, in the main body part 10 according to this embodiment, due to the quality of the materials of the warp 1 and the weft 2 (in particular, the thicknesses of the elastic yarn 1c and the weft ground yarn 2a) described above and the number of times of picking (the number) of the weft 2 described above, it is possible to set the maximum elongation in the warp direction (the longitudinal direction L) to be 60%. Further, the main body part 10 according to this embodiment has a mixing ratio of nylon: 47%, polyester: 44%, and polyurethane: 9%. However, there is no limitation to this mixing ratio.

Further, in the first anchor part 20 according to this embodiment, due to the quality of the materials of the warp 1 and the weft 2 (in particular, the thicknesses of the elastic yarn 1c and the weft ground yarn 2a) described above and the number of times of picking (the number) of the weft 2 described above, it is possible to set the maximum elongation in the warp direction (the longitudinal direction L) to be 95%.

Further, the first anchor part 20 according to this embodiment has a mixing ratio of nylon: 66%, polyester: 24%, and polyurethane: 10%. However, there is no limitation to this mixing ratio.

Further, in the main body part 10, in order to configure a crossing portion below the knee and a lower anchor, the lengths of portions (the first supporting part 12 and the second supporting part 13) which cross each other below the knee of a wearer, and the length of a portion (the second anchor part 211) which circles at least half around the lower leg of the wearer below the popliteal region of the wearer are required, and although there is an individual difference in the circumference of the knee or the thickness of the lower leg according to gender, age, or the like, it is conceivable that the length of the main body part 10 is set to in, for example, a range of 44 cm to 52 cm (for example, S-size: 44 cm, M-size: 48 cm, L-size: 52 cm).

Further, in the first anchor part 20 according to this embodiment, in order to circle around the thigh of a wearer, for example, it is preferable to set the length of the band-shaped body to be in a range of 29 cm to 37 cm (for example, S-size: 29 cm, M-size: 33 cm, L-size: 37 cm).

Further, with respect to the bag-shaped part 71 of the connection part 70 according to this embodiment, a 100% polyester double Russell fabric (for example, part number "7200SK" of Inoue Knit Co., Ltd.) is used, and the double Russell fabric having a rectangular shape (for example, longitudinal size: 17.5 cm, transverse size: 6 cm) is folded in half with the support 72 sandwiched therebetween and is sewn at a peripheral edge portion excluding the folded portion, whereby a structure containing the support 72 is made.

Further, as long as it is a fabric having shock-absorbing properties, the bag-shaped part 71 is not limited to the double Russell fabric, and for example, a fabric obtained by bonding other fabrics to both sides of neoprene, a fabric obtained by bonding other fabrics to both sides of urethane foam, or the like is also acceptable.

Further, the left bag-shaped part 71a (the right bag-shaped part 71b) according to this embodiment is joined (for example, sewn) from the back fabric side with an upper side of the left bag-shaped part 71a (the right bag-shaped part 71b) aligned with the upper side 20d of the first anchor part 20, at a position where the distance from one end 20a (the other end 20b) of the first anchor part 20 to the center line of the left bag-shaped part 71a (the right bag-shaped part 71b) is about 6 cm, and is joined (for example, sewn) from the back fabric side with a lower side of the left bag-shaped part 71a (the right bag-shaped part 71b) aligned with a lower side of the main body part 10, at a position where the distance from one end 10a (the other end 10b) of the main body part 10 to the center line of the left bag-shaped part 71a (the right bag-shaped part 71b) is about 14.5 cm. However, it is preferable that the joining position of the bag-shaped part 71 (the left bag-shaped part 71a and the right bag-shaped part 71b) is appropriately set in consideration of the maximum elongation in the warp direction (the longitudinal direction L) of each of the main body part 10 and the first anchor part 20.

That is, the distance between an upper end of the left bag-shaped part 71a (the left support 72a) and an upper end of the right bag-shaped part 71b (the right support 72b) and the distance between a lower end of the left bag-shaped part 71a (the left support 72a) and a lower end of the right bag-shaped part 71b (the right support 72b) are not limited to being the same as each other and may have different (wider or narrower) configurations, and it is preferable that the distances are appropriately set in consideration of the maximum elongation in the warp direction (the longitudinal direction L) of each of the main body part 10 and the first anchor part 20.

Further, with respect to the support 72 which is contained in the bag-shaped part 71 according to this embodiment, a PP plate containing 100% polypropylene (PP) and having a thickness in a range of 1.2 mm to 4.0 mm is used. However, there is no limitation to the PP plate having the plate thickness and the quality of material, and for example, polyethylene foam (for example, "Sunpelca (registered trademark)" or "Belporen (foamed polyethylene)"), a hard vinyl chloride plate, a hard gum (rubber) plate, a polycarbonate plate, or the like is also acceptable. Further, the support 72 according to this embodiment is not limited to a plate-shaped body and may be, for example, a columnar body such as a circular column or a rectangular column, a columnar body having a hollow or a groove extending in a longitudinal direction, a columnar body with a separate member fitted into a hollow or a groove extending in a longitudinal direction, or the like.

In particular, the support 72 contained in the bag-shaped part 71 is a plate-shaped body having flexibility which is bent in a direction perpendicular to a principal surface (is not easily bent in a direction horizontal to a principal surface), and in this way, in a case where a wearer has flexed the knee joint, due to the restoring force of the support 72 bent in a direction perpendicular to the principal surface, a force trying to return the knee joint of the wearer to a normal position acts.

Further, the bag-shaped part 71 (the left bag-shaped part 71a and the right bag-shaped part 71b) is joined at the back fabric sides of the main body part 10 and the first anchor part 20, whereby the connection part 70 (the support 72) is provided on the inside (the wearer side) with respect to the main body part 10 and the first anchor part 20 in a state where the knee joint supporter 200 has been worn.

For this reason, it is possible to press an upper end and a lower end of the connection part 70 (the bag-shaped part 71 and the support 72) with the main body part 10 and the first anchor part 20, and thus it is possible to prevent the protrusion of the upper end and the lower end of the connection part 70 (the bag-shaped part 71 and the support 72).

In particular, the upper end of the connection part 70 (the bag-shaped part 71) and the first anchor part 20 are joined to each other with the upper side 20d of the first anchor part 20 folded from the upper side 20d side of the first anchor part 20 to the back fabric side and the upper end of the connection part 70 (the bag-shaped part 71) gripped by the folded portion of the first anchor part 20, whereby the upper end of the bag-shaped part 71 is reinforced, and thus it is possible to prevent damage to the upper end of the bag-shaped part 71 by the support 72.

Next, a method of wearing the knee joint supporter 200 shown in FIG. 14 will be described by using FIG. 15.

In addition, in the following description, a case of wearing the knee joint supporter 200 on the right knee of a wearer will be described. However, in a case of wearing the knee joint supporter 200 on the left knee of the wearer, wearing is performed with the "right knee", the "outer surface of the lower leg", and the "inner surface of the lower leg" respectively replaced by the "left knee", the "inner surface of the lower leg", and the "outer surface of the lower leg".

A wearer fastens the first anchor part 20 around the thigh by disposing the first anchor part 20 in an extended state at the thigh by winding the first anchor part 20 around the thigh with the right hand while pressing one end 20a of the first anchor part 20 with the left hand with one end 20a of the first anchor part 20 fitted to the center of the thigh in the vicinity of the kneecap, and making the hook face 43 of the second engaging part 40 which is located at the other end 20b of the first anchor part 20 be engaged with the loop face 21 of the first anchor part 20, as shown in FIG. 15(a).

In this case, the left connection part 70 (the left bag-shaped part 71a and the left support 72a) is disposed between the patella 300 and the sartorius muscle of the wearer, and the right connection part 70 (the right bag-shaped part 71b and the right support 72b) is disposed between the patella 300 and the iliotibial band of the wearer.

Then, the wearer pulls the first supporting part 12 of the main body part 10 while gripping one end 10a of the main body part 10 (the first supporting part 12) with the right hand and disposes the first supporting part 12 of the main body part 10 in an extended state from below the part corresponding to the patella 300 of the right knee to the right side.

Then, the wearer makes the hook face 63 of the third engaging part 60 which is located at one end 10a of the main body part 10 be engaged with the loop face 21 of the first anchor part 20, as shown in FIG. 15(b). In this case, the first supporting part 12 is superimposed on the right connection part 70 (the right bag-shaped part 71b and the right support 72b), thereby pressing the right connection part 70.

Then, the wearer grips the other end 10b of the main body part 10 (the second supporting part 13) with the left hand and disposes the second supporting part 13 of the main body part 10 in an extended state on the left side while crossing the first supporting part 12 below the part corresponding to the patella 300 of the right knee.

Finally, the wearer makes the hook face 33 of the first engaging part 30 which is located at the other end 10b of the main body part 10 be engaged with the loop face 21 of the first anchor part 20, as shown in FIGS. 15(c) and 15(d), whereby the wearing is completed. In this case, the second supporting part 13 is superimposed on the left connection part 70 (the left bag-shaped part 71a and the left support 72a), thereby pressing the left connection part 70.

In addition, in the wearing method of the knee joint supporter 200 described above, a case where after the first supporting part 12 of the main body part 10 is disposed from the right side of the part corresponding to the patella 300 of the right knee, the second supporting part 13 of the main body part 10 is disposed from the left side of the part corresponding to the patella 300 of the right knee has been described. However, the first supporting part 12 of the main body part 10 may be disposed from the right side of the part corresponding to the patella 300 of the right knee after the second supporting part 13 of the main body part 10 is disposed from the left side of the part corresponding to the patella 300 of the right knee.

As described above, in the knee joint supporter 200, the main body part 10 (the first supporting part 12 and the second supporting part 13) fixes the patella 300 (the knee joint) of a wearer so as to wrap the patella 300 (the knee joint) while raising the patella 300 (the knee joint) from below toward the thigh side from the lower leg side and supports the medial collateral ligament and the medial collateral ligament of the wearer, whereby it is possible to smoothly assist in the movement of the quadriceps muscle, and it is possible to reduce a burden on the knee by suppressing the deflection to right and left of the knee.

Further, in the knee joint supporter 200, the main body part 10 (the first supporting part 12 and the second supporting part 13) grips and presses the knee joint of a wearer from the right and left and limits extra extension of the knee ligament (the medial collateral ligament and the medial collateral ligament) of the wearer, whereby it is possible to suppress the abrasion of the cartilage or the inflammation of the ligament of the knee joint and prevent damage to the knee joint.

In particular, the knee joint supporter 200 according to this embodiment is provided with the connection parts 70, whereby even in a state where the second anchor part 211 is pulled by the first supporting part 12 and the second supporting part 13, the distance between the first anchor part 20 and the second anchor part 211 is maintained, and the crossing portion of the first supporting part 12 and the second supporting part 13 moves upward based on the extension of the first supporting part 12 and the second supporting part 13 while preventing sliding-up of the second anchor part 211, and thus it is possible to sufficiently fulfill a function of pushing up the patella 300 by the crossing portion.

Further, the mounting of a knee supporter provided with two band-shaped supporting parts equivalent to the first supporting part 12 and the second supporting part 13 of the knee joint supporter 200 is effective as a method for supporting the knee joint of a wearer. That is, due to mounting the knee supporter (for example, the knee joint supporter 200) so as to raise the patella of a wearer from the lower side to the upper side by disposing the two band-shaped supporting parts (for example, the first supporting part 12 and the second supporting part 13) on both right and left sides after crossing at the lower side of the part corresponding to the patella of the wearer, the two band-shaped supporting parts support the patella of the wearer so as to raise the patella from the lower side to the upper side with the crossing portion of the two band-shaped supporting parts as a point of action on the patella of the wearer while the two band-shaped supporting parts grip the patella of the wearer from the right and left, and therefore, it is possible to exhibit the operation and effects of reducing a burden on the knee region of the wearer by smoothly assisting in the movement of the quadriceps muscle.

Further, the mounting of a knee supporter in which a band-shaped anchor part having a loop face, which is equivalent to the first anchor part 20 of the knee joint supporter 200, is provided at the knee supporter provided with the two band-shaped supporting parts is more effective as a method for supporting the knee joint of a wearer. That is, due to mounting the knee supporter so as to raise the patella from the lower side to the upper side by making one end of each of the two band-shaped supporting parts (for example, the first supporting part 12 and the second supporting part 13) be engaged with the loop face of the band-shaped anchor part (for example, the first anchor part 20) fixed to the thigh of a wearer, the knee supporter is reliably fixed to the position of the knee joint of the wearer, and therefore, it is possible to more effectively exhibit the operation and effects of the two band-shaped supporting parts.

In addition, the knee joint supporter 200 according to this embodiment has been described using the main body part 10 in which the second anchor part 211, the first supporting part 12, and the second supporting part 13 are integrally woven to be continuous. However, as shown in FIG. 18, the main body part 10 is also acceptable in which the second anchor part 211, the first supporting part 12, and the second supporting part are woven as separate members and each of the first supporting part 12 and the second supporting part 13 is joined to and integrated with the second anchor part 211.

In this case, the second anchor part 211 is woven in a fabric having a loop face 211*e* of a touch fastener, and a fourth engaging part 80 having a hook face of a touch fastener, which is detachably stuck to the loop face 211*e* of the second anchor part 211, is provided on the back ground face side of one end 211*a* or the other end 211*b* (in FIG. 18(*a*), the other end 211*b*).

In the case of this form, as shown in FIG. 18(*b*), the second anchor part 211 has a length which circles around the lower leg of a wearer, whereby it is possible to enhance an anchor function by the second anchor part 211.

Further, in the knee joint supporter 200 according to this embodiment, as shown in FIG. 19, an annular grip 25 into which the other end 20*b* of the first anchor part 20 can be inserted may be provided on the front ground face (the loop face 21) side of one end 20*a* of the first anchor part 20.

In this case, in the mounting of the first anchor part 20 in the wearing method of the knee joint supporter 200, as shown in FIG. 19(*b*), a wearer winds the first anchor part 20 around the thigh of the wearer and inserts the second engaging part 40 which is located at the other end 20*b* of the first anchor part 20 into the grip 25 which is located at one end 20*a* of the first anchor part 20.

Then, the wearer fastens the first anchor part 20 around the thigh by pulling the other end 20*b* (the second engaging part 40) and one end 20*a* (the grip 25) in the opposite directions in a state of gripping the other end 20*b* (the second engaging part 40) of the first anchor part 20 with the left hand and gripping one end 20*a* (the grip 25) of the first anchor part 20 with the right hand, and then making the hook face 43 of the second engaging part 40 be engaged with the loop face 21 of the first anchor part 20.

In this manner, in a case of pulling one end 20*a* of the first anchor part 20, which is not easily gripped due to the second engaging part 40 not being present therein, with the right hand, the grip 25 is easily hooked to and gripped with the finger of a wearer, and thus it is possible to assist in the pulling by a wearer such as a powerless woman or aged person.

Further, in the knee joint supporter 200 according to this embodiment, a case where the pattern 14 described in the first embodiment is not formed in the main body part 10 has been described. However, as necessary, the pattern 14 may be formed in the main body part 10 by using a jacquard needle loom.

Fourth Embodiment of the Present Invention

Figure 20:
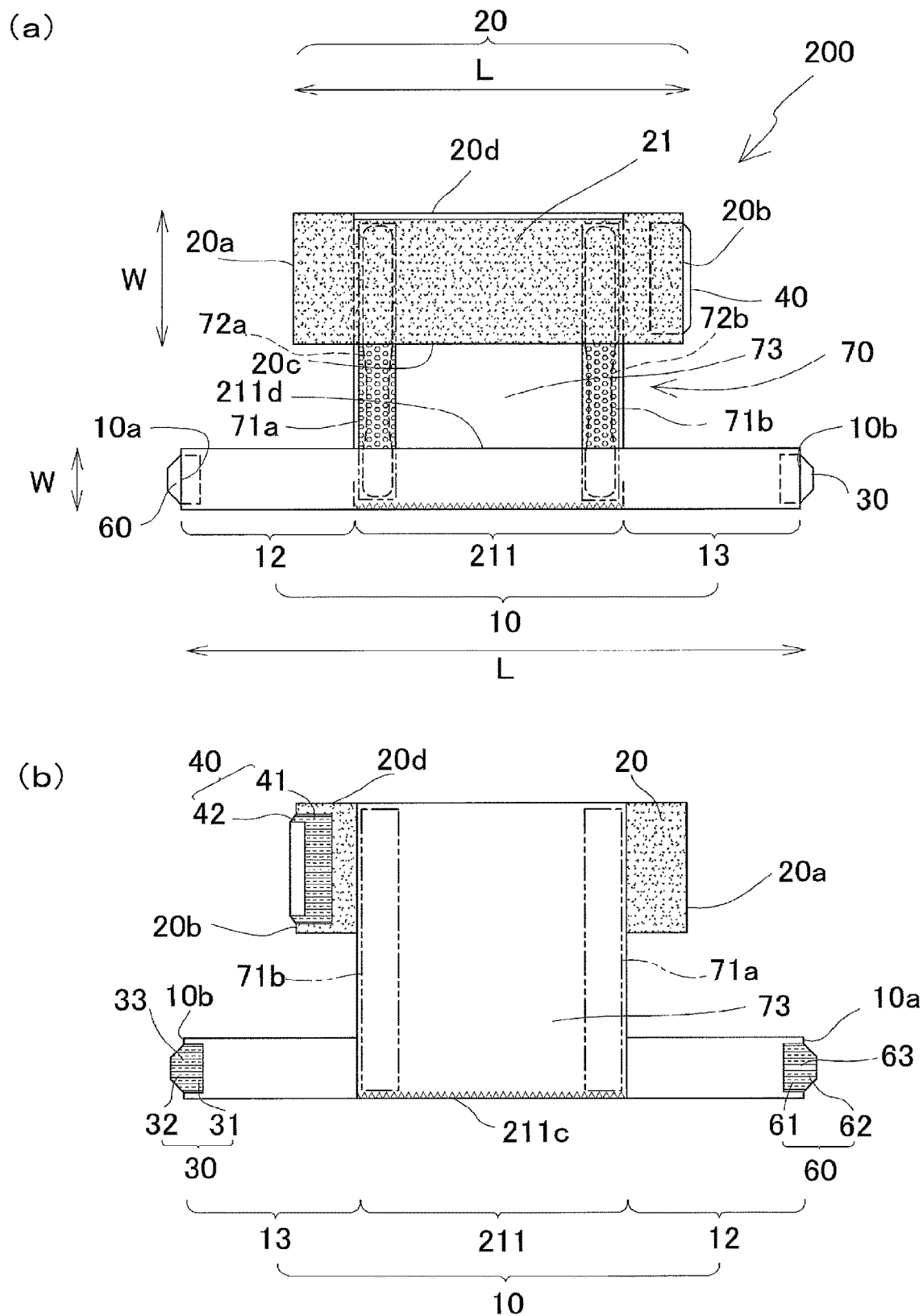
FIG. 20(a) is a front view showing a schematic configuration of a knee joint supporter according to a fourth embodiment.
FIG. 20(b) is a back view of the knee joint supporter shown in FIG. 15(a).

FIG. 20(*a*) is a front view showing a schematic configuration of a knee joint supporter according to a fourth embodiment, and FIG. 20(*b*) is a back view of the knee joint supporter shown in FIG. 15(*a*). In FIG. 20, the same reference numerals as those in FIGS. 1 to 3 and 14 to 19 denote identical or corresponding parts, and description thereof is omitted.

The connection parts 70 according to this embodiment are the pair of left and right bag-shaped parts 71 (the left bag-shaped part 71*a* and the right bag-shaped part 71*b*) each containing the support 72, and a covering part 73 which covers an area surrounded by the pair of left and right bag-shaped parts 71, the lower side 20*c* of the first anchor part 20, and an upper side 211*d* of the second anchor part 211 (is sewn to the first anchor part 20 and the second anchor part 211, opens the kneecap side of a wearer, and covers the popliteal region and both sides of the knee of the wearer), as shown in FIG. 20, and are disposed in a taut state at the popliteal region of the wearer from both sides of the part corresponding to the patella of the wearer.

Further, the covering part 73 according to this embodiment is made of a rectangular fabric overlapping the area surrounded by the first anchor part 20, the second anchor part 211, and the bag-shaped parts 71 (the left bag-shaped part 71*a* and the right bag-shaped part 71*b*) and is sewn to the back ground face side of the knee joint supporter 200.

Further, with respect to the covering part 73 according to this embodiment, a cloth which is a cotton-blended power net (for example, part number "CI1543" (mixing ratio: nylon 60%, (yarn count: 56 decitexes), cotton 23%, (yarn count: 40 single yarn), and polyurethane 17% (thread count: 310 decitexes) of Inoue knit Co., Ltd.) is used.

However, as long as it is a fabric having stretchability, the covering part 73 is not limited to the cotton-blended power net and may be, for example, a cloth such as: a two-way tricot raised fabric (for example, part number "NS4426K" (mixing ratio: polyester 85% and polyurethane 15%, warp knitting machine gauge number: 28 gauges, weight per unit area: 250 g/m$^2$, thread for weaving: polyester yarn obtained by twisting 36 pieces of filaments together and having a thickness of 56 decitexes, and polyurethane yarn having a thickness of 44 decitexes) of Inoue knit Co., Ltd.) which is a warp knitting fabric or a weft knitting fabric, has raising on the back ground face, and extends in a longitudinal direction and a transverse direction; a warp knitting two-way tricot fabric (as a thread for weaving, for example, part number "3100" (mixing ratio: polyester 83% and polyurethane 17%) of Inoue knit Co., Ltd., or part number "5100" (mixing ratio: nylon 85% and polyurethane 15%) of Inoue knit Co., Ltd.); a 100% polyester double Russell fabric (for example, part number "7200SK" of Inoue Knit Co., Ltd.); or a circular knitting bare plain fabric (as a thread for weaving, for example, part number "YG103" (mixing ratio: cotton 95% and polyurethane 5%) of Inoue knit Co., Ltd.).

Further, the fourth embodiment is different from the third embodiment only in that the fourth embodiment is provided with the covering part 73, and exhibits the operation and effects which are the same as those in the third embodiment except for the operation and effects by the covering part 73, which will be described later.

In the knee joint supporter 200 according to this embodiment, the covering part 73 is provided on the inside (the wearer side) with respect to the first anchor part 20, the second anchor part 211, and the bag-shaped parts 71 (the supports 72), whereby in a case where a wearer has flexed the knee joint, the covering part 73 serves as a shock-absorbing material, and thus it is possible to alleviate a feeling of discomfort due to the skin of the popliteal region being sandwiched between the first anchor part 20 and the second anchor part 211 which approach each other.

Further, in the covering part 73 according to this embodiment, in the area overlapping the first anchor part 20, the covering part 73 is sewn at the upper side 20d of the first anchor part 20 and both sides and is not sewn at the lower side 20c of the first anchor part 20, and in the area overlapping the second anchor part 211, the covering part 73 is sewn at a lower side 211c of the second anchor part 211 and some of the lower sides of both sides and is not sewn at the upper side 211d of the second anchor part 211.

Due to these sewing positions, the covering part 73 in which the maximum elongations of the first anchor part 20 and the second anchor part 211 are different from each other is prevented from following the extension movements of the first anchor part 20 and the second anchor part 211 as much as possible, and thus it is possible to suppress the occurrence of wrinkles of the covering part 73.

In particular, in the knee joint supporter 200 according to this embodiment, as shown in FIG. 20(*a*), the covering part 73 is folded and joined to the front fabric side at the upper side 20d of the first anchor part 20, whereby the covering part 73 bent at the upper side 20d of the first anchor part 20 serves as a shock-absorbing material, and thus an edge end portion of the first anchor part 20 (the upper side 20d) is prevented from coming into direct contact with the bare skin on the back side of the thigh of a wearer and it is possible to alleviate the pressing force from the edge end portion of the first anchor part 20 (the upper side 20d).

Further, in the knee joint supporter 200 according to this embodiment, the upper side 20d of the first anchor part 20 is folded from the upper side 20d side of the first anchor part 20 to the back fabric side, and the upper ends of the covering part 73 and the connection parts 70 (the bag-shaped parts 71) are joined to be gripped with the folded portion of the first anchor part 20, whereby the upper ends of the bag-shaped parts 71 are reinforced, and thus it is possible to prevent damage to the upper ends of the bag-shaped parts 71 by the supports 72.

Further, in the knee joint supporter 200 according to this embodiment, the connection part 70 composed of the bag-shaped part 71 containing the support 72, and the covering part 73 has been described. However, if it is a configuration in which the first anchor part 20 and the main body part 10 (the second anchor part 211) are integrated, the connection part 70 composed of the covering part 73 is also acceptable.

Further, a case where each of the knee supporters (the knee joint bandages 100 and the knee joint supporters 200) according to the first embodiment to the fourth embodiment is directly wound around the bare skin has been described. However, with respect to the knee joint on which, for example, a knee joint supporter disclosed in Pamphlet of International Publication No. WO/2011/090194 or an innerwear (spats, stockings, or tights and panty-stockings) having a knee part is worn, the knee supporter (the knee joint bandage 100 or the knee joint supporter 200) is wound on the knee joint supporter or the innerwear, thereby eliminating the slip of the knee supporter (the knee joint bandage 100 or the knee joint supporter 200) with respect to the bare skin, whereby it is possible to improve the operation and effects of the knee supporter (the knee joint bandage 100 or the knee joint supporter 200).

Further, in a case where each of the knee joint bandages 100 according to the first embodiment and the second embodiment is wound on the innerwear, it is also possible to provide the knee joint bandage 100 and the innerwear as a set.

Further, in a case where each of the knee joint bandages 100 according to the first embodiment and the second embodiment is wound on the innerwear (an innerwear in which the maximum elongation is low is preferable), as an aspect of the knee joint bandage 100, the first anchor part 20 of the knee joint bandage 100 is removed from the main body part 10 and one end 10a of the main body part 10 is sewn to the outer surface or the inner surface above the knee part of the innerwear, whereby it is possible to make the thigh part circumference of the innerwear function as the first anchor part 20.

REFERENCE SIGNS LIST

1: warp
1*a*: warp ground yarn (first warp ground yarn)
1*b*: pile yarn
1*c*: elastic yarn
1*d*: second warp ground yarn
2: weft
2*a*: weft ground yarn
2*b*: fusion yarn
10: main body part
10*a*: one end
10*b*: other end
10*c*: one side
10*d*: loop face
11: winding part
12: first supporting part
13: second supporting part
14: pattern
20: first anchor part
20*a*: one end
20*b*: other end
20*c*: lower side
20*d*: upper side
21: loop face
22: center mark
23: intersection point
24: slit
25: grip
30: first engaging part
31: rectangular portion
32: isosceles trapezoid portion
33: hook face
40: second engaging part
41: rectangular portion
42: isosceles trapezoid portion
43: hook face
50: joining portion
60: third engaging part
61: rectangular portion
62: isosceles trapezoid portion
63: hook face
70: connection part
71*a*: left bag-shaped part
71*b*: right bag-shaped part
72: support
72*a*: left support
72*b*: right support
73: covering part
80: fourth engaging part
100: knee joint bandage
200: knee joint supporter
211: second anchor part
211*a*: one end
211*b*: other end 211c: lower side
211d: upper side
211e: loop face
300: patella

The invention claimed is:

1. A knee joint supporter, comprising:
a first anchor part comprising a woven fabric and having a loop face;
a main body part comprising a band-shaped fabric and including a second anchor part, a first supporting part, and a second supporting part;
a plurality of connection parts joining the first anchor part and the second anchor part such that the connection parts are connecting the first anchor part and the main body part;
a first engaging part joined to an end portion of the second supporting part and having a hook face such that the hook face detachably sticks to the loop face of the first anchor part;
a second engaging part joined to one end of the first anchor part and having a hook face such that the hook face detachably sticks to the loop face of the first anchor part; and
a third engaging part joined to an end portion of the first supporting part and having a hook face such that the hook face detachably sticks to the loop face of the first anchor part,
wherein the first anchor part is configured to fasten around a thigh of a wearer, and the main body part is formed such that the second anchor part is configured to extend at least below a popliteal region of the wearer, the first supporting part is configured to extend on one side from below a part corresponding to a patella of the wearer, and the second supporting part is configured to extend on the other side of the part corresponding to the patella of the wearer and is configured to cross the first supporting part below the part corresponding to the patella of the wearer.

2. The knee joint supporter according to claim 1, wherein the main body part has the first supporting part on one end side of the main body part, the second supporting part on the other end side of the main body part, the second anchor part between the first supporting part and the second supporting part, and the main body part has a straight shape having an equal width.

3. The knee joint supporter according to claim 2, wherein the plurality of connection parts comprises a pair of left and right bag-shaped parts each comprising a support and is configured to extend on both sides of the part corresponding to the patella of the wearer.

4. The knee joint supporter according to claim 3, wherein the main body part has a maximum elongation in a range of 40% to 80% in a longitudinal direction of the main body part.

5. The knee joint supporter according to claim 3, wherein the first anchor part has a width which is wider than a width of the second anchor part of the main body part.

6. The knee joint supporter according to claim 2, wherein the plurality of connection parts comprises a pair of left and right bag-shaped parts each comprising a support, and a covering part configured to cover an area surrounded by the pair of left and right bag-shaped parts, a lower side of the first anchor part, and an upper side of the second anchor part, and is configured to extend on the popliteal region of the wearer from both sides of the part corresponding to the patella of the wearer.

7. The knee joint supporter according to claim 6, wherein the main body part has a maximum elongation in a range of 40% to 80% in a longitudinal direction of the main body part.

8. The knee joint supporter according to claim 6, wherein the first anchor part has a width which is wider than a width of the second anchor part of the main body part.

9. The knee joint supporter according to claim 2, wherein the main body part has a maximum elongation in a range of 40% to 80% in a longitudinal direction of the main body part.

10. The knee joint supporter according to claim 2, wherein the first anchor part has a width which is wider than a width of the second anchor part of the main body part.

11. The knee joint supporter according to claim 1, wherein the plurality of connection parts comprises a pair of left and right bag-shaped parts each comprising a support and is configured to extend on both sides of the part corresponding to the patella of the wearer.

12. The knee joint supporter according to claim 11, wherein the main body part has a maximum elongation in a range of 40% to 80% in a longitudinal direction of the main body part.

13. The knee joint supporter according to claim 11, wherein the first anchor part has a width which is wider than a width of the second anchor part of the main body part.

14. The knee joint supporter according to claim 1, wherein the plurality of connection parts comprises a pair of left and right bag-shaped parts each comprising a support, and a covering part configured to cover an area surrounded by the pair of left and right bag-shaped parts, a lower side of the first anchor part, and an upper side of the second anchor part, and is configured to extend on the popliteal region of the wearer from both sides of the part corresponding to the patella of the wearer.

15. The knee joint supporter according to claim 14, wherein the main body part has a maximum elongation in a range of 40% to 80% in a longitudinal direction of the main body part.

16. The knee joint supporter according to claim 14, wherein the first anchor part has a width which is wider than a width of the second anchor part of the main body part.

17. The knee joint supporter according to claim 1, wherein the main body part has a maximum elongation in a range of 40% to 80% in a longitudinal direction of the main body part.

18. The knee joint supporter according to claim 1, wherein the first anchor part has a width which is wider than a width of the second anchor part of the main body part.

* * * * *